(12) United States Patent
Bailey et al.

(10) Patent No.: US 11,457,881 B2
(45) Date of Patent: Oct. 4, 2022

(54) ANATOMICAL IMAGING SYSTEM WITH SCANNING TABLE MOVABLE ALONG THE X-AXIS AND/OR SCANNING TABLE MOVABLE ALONG THE Y-AXIS AND THE Z-AXIS

(71) Applicant: Samsung Electronics Co., Ltd., Gyeonggi-do (KR)

(72) Inventors: Eric Bailey, North Hampton, NH (US); Andrew Tybinkowski, Topsfield, MA (US); Marshal Doughty, Weymouth, MA (US)

(73) Assignee: Samsung Electronics Co., Ltd.

( * ) Notice: Subject to any disclaimer, the term of this patent is extended or adjusted under 35 U.S.C. 154(b) by 263 days.

(21) Appl. No.: 16/000,119

(22) Filed: Jun. 5, 2018

(65) Prior Publication Data

US 2019/0069855 A1    Mar. 7, 2019

Related U.S. Application Data

(63) Continuation of application No. 14/825,280, filed on Aug. 13, 2015, now Pat. No. 9,986,954.

(60) Provisional application No. 62/036,774, filed on Aug. 13, 2014, provisional application No. 62/036,787, filed on Aug. 13, 2014.

(51) Int. Cl.
| | |
|---|---|
| *A61B 6/04* | (2006.01) |
| *A61B 6/03* | (2006.01) |
| *A61B 6/02* | (2006.01) |
| *A61B 6/00* | (2006.01) |

(52) U.S. Cl.
CPC ............ *A61B 6/0487* (2020.08); *A61B 6/027* (2013.01); *A61B 6/032* (2013.01); *A61B 6/035* (2013.01); *A61B 6/0407* (2013.01); *A61B 6/0442* (2013.01); *A61B 6/4405* (2013.01)

(58) Field of Classification Search
CPC ........... A61B 6/04; A61B 6/027; A61B 6/032; A61B 6/035; A61G 6/0487
USPC ...................................... 5/601, 600
See application file for complete search history.

(56) References Cited

U.S. PATENT DOCUMENTS

| | | | |
|---|---|---|---|
| 3,588,500 A | 6/1971 | Koerner | |
| 3,967,126 A | 6/1976 | Otto, Jr. | |
| 4,205,233 A | 5/1980 | Craig et al. | |
| 4,613,122 A * | 9/1986 | Manabe | ................. A61G 7/012 |
| | | | 5/601 |
| 4,761,000 A | 8/1988 | Fisher et al. | |
| 5,077,780 A | 12/1991 | Lee, Jr. | |
| 5,475,885 A | 12/1995 | Ishikawa | |
| 5,590,429 A | 1/1997 | Boomgaarden et al. | |
| 6,094,760 A | 8/2000 | Nonaka et al. | |
| 6,405,072 B1 | 6/2002 | Cosman | |
| 8,578,529 B2 | 11/2013 | Miyano et al. | |
| 2004/0057557 A1 * | 3/2004 | Nafstadius | ............... A61B 6/04 |
| | | | 378/209 |

(Continued)

FOREIGN PATENT DOCUMENTS

| | | |
|---|---|---|
| CN | 102413768 | 4/2012 |
| DE | 1219625 | 6/1966 |

(Continued)

*Primary Examiner* — Fredrick C Conley
(74) *Attorney, Agent, or Firm* — Pandiscio & Pandiscio

(57) ABSTRACT

A novel scanning table for use with a scanning machine, the novel scanning table being movable along the X-axis and/or movable along the Y-axis and the Z-axis.

27 Claims, 37 Drawing Sheets

(56) References Cited

U.S. PATENT DOCUMENTS

| | | | |
|---|---|---|---|
| 2005/0129181 A1 | 6/2005 | Shinoda | |
| 2005/0204472 A1* | 9/2005 | Gagneur | A61B 5/0555 5/601 |
| 2006/0241408 A1* | 10/2006 | Yakubovsky | A61B 6/0407 600/429 |
| 2012/0023671 A1 | 2/2012 | Miyano et al. | |
| 2013/0322603 A1 | 12/2013 | Kurachi et al. | |
| 2014/0098934 A1 | 4/2014 | Kondo | |
| 2014/0210468 A1* | 7/2014 | Xu | A61B 6/0487 324/309 |

FOREIGN PATENT DOCUMENTS

| | | |
|---|---|---|
| DE | 2803312 | 8/1979 |
| DE | 4317264 | 12/1994 |
| EP | 0457248 | 11/1991 |
| EP | 0923922 | 6/1999 |
| EP | 2984989 | 2/2016 |
| FR | 2749503 | 12/1997 |
| JP | H06 54842 | 3/1994 |
| JP | 2013-039303 | 2/2013 |
| KR | 10-2014-0085332 | 7/2014 |
| WO | WO 2001/049234 | 7/2001 |

\* cited by examiner

ANATOMICAL IMAGING SYSTEM WITH SCANNING TABLE MOVABLE ALONG THE X-AXIS AND/OR SCANNING TABLE MOVABLE ALONG THE Y-AXIS AND THE Z-AXIS

REFERENCE TO PENDING PRIOR PATENT APPLICATIONS

This patent application is a continuation of pending prior U.S. patent application Ser. No. 14/825,280, filed Aug. 13, 2015 by Samsung Electronics Co., Ltd. for ANATOMICAL IMAGING SYSTEM WITH SCANNING TABLE MOVABLE ALONG THE X-AXIS AND/OR SCANNING TABLE MOVABLE ALONG THE Y-AXIS AND THE Z-AXIS, which patent application in turn:

(i) claims benefit of prior U.S. Provisional Patent Application Ser. No. 62/036,774, filed Aug. 13, 2014 by Neurologica Corp. and Eric Bailey et al. for ANATOMICAL IMAGING SYSTEM WITH SCANNING TABLE MOVABLE ALONG THE X-AXIS; and (ii) claims benefit of prior U.S. Provisional Patent Application Ser. No. 62/036,787, filed Aug. 13, 2014 by Neurologica Corp. and Eric Bailey et al. for ANATOMICAL IMAGING SYSTEM WITH SCANNING TABLE MOVABLE ALONG THE Y-AXIS AND THE Z-AXIS.

The three (3) above-identified patent applications are hereby incorporated herein by reference.

FIELD OF THE INVENTION

This invention relates to imaging systems in general, and more particularly to anatomical imaging systems.

BACKGROUND OF THE INVENTION

In many situations it can be desirable to image the interior of opaque objects. By way of example but not limitation, in the medical field, it can be desirable to image the interior of a patient's body so as to allow viewing of internal structures without physically penetrating the skin.

Computerized Tomography (CT) has emerged as a key imaging modality in the medical field. CT imaging systems generally operate by directing X-rays into the body from a variety of positions, detecting the X-rays passing through the body, and then processing the detected X-rays so as to build a three-dimensional (3D) data set and a 3D computer model of the patient's anatomy. The 3D data set and 3D computer model can then be visualized so as to provide images (e.g., slice images, 3D computer images, etc.) of the patient's anatomy.

By way of example but not limitation, and looking now at FIGS. 1 and 2, there is shown an exemplary CT imaging system 5. CT imaging system 5 generally comprises a torus 10 which is supported by a base 15. A center opening 20 is formed in torus 10. Center opening 20 receives the patient anatomy which is to be scanned.

Looking next at FIG. 3, torus 10 generally comprises a fixed gantry 22, a rotating disc 23, an X-ray tube assembly 25 and an X-ray detector assembly 30. More particularly, fixed gantry 22 is disposed concentrically about center opening 20. Rotating disc 23 is rotatably mounted to fixed gantry 22. X-ray tube assembly 25 and X-ray detector assembly 30 are mounted to rotating disc 23 in diametrically-opposing relation, such that an X-ray beam 40 (generated by X-ray tube assembly 25 and detected by X-ray detector assembly 30) is passed through the patient anatomy disposed in center opening 20. Inasmuch as X-ray tube assembly 25 and X-ray detector assembly 30 are mounted on rotating disc 23 so that they are rotated concentrically about center opening 20, X-ray beam 40 will be passed through the patient's anatomy along a full range of radial positions, so as to enable CT imaging system 5 to create a "slice" image of the anatomy penetrated by the X-ray beam. Furthermore, by moving the patient and CT imaging system 5 relative to one another during scanning, a series of slice images can be acquired, and thereafter appropriately processed, so as to create a 3D data set of the scanned anatomy and a 3D computer model of the scanned anatomy. In practice, it is common to configure X-ray detector assembly 30 so that multiple slices of images (e.g., 8 slices, 16 slices, 32 slices, etc.) may be acquired with each rotation of rotating disc 23, whereby to speed up the acquisition of scan data.

In practice, it is now common to effect helical scanning of the patient's anatomy so as to generate a 3D data set of the scanned anatomy, which can then be processed to build a 3D computer model of the scanned anatomy. The 3D data set and 3D computer model can then be visualized so as to provide images (e.g., slice images, 3D computer images, etc.) of the patient's anatomy.

The various electronic hardware and software for controlling the operation of rotating disc 23, X-ray tube assembly 25 and X-ray detector assembly 30, as well as for processing the acquired scan data so as to generate the desired slice images, 3D data set and 3D computer model, may be of the sort well known in the art and may be located in torus 10 and/or base 15.

In many cases CT imaging system 5 is intended to be stationary, in which case base 15 of CT imaging system 5 is set in a fixed position on the floor of a room and a special motorized scanning table is provided to move the patient relative to CT imaging system 5 during scanning. More particularly, with a stationary CT imaging system 5, the patient is brought to the location of CT imaging system 5, the patient is placed on the motorized scanning table, and then the motorized scanning table is used to move the patient relative to CT imaging system 5 (i.e., to advance the patient into center opening 20 of CT imaging system 5) so that some or all of the length of the patient may be scanned by CT imaging system 5.

In other cases CT imaging system 5 is intended to be mobile so that the CT imaging system may be brought to the patient and the patient scanned at the patient's current location, rather than requiring that the patient be transported to the location of the CT imaging system. Scanning the patient with a mobile CT imaging system 5 can be highly advantageous, since it can reduce delays in patient scanning (e.g., the patient can be scanned in an emergency room rather than waiting to be transported to the radiology department) and/or it can allow the patient to be scanned without requiring movement of the patient (e.g., the patient can be scanned at their bedside in an intensive care unit, "ICU"). To this end, and looking now at FIGS. 4 and 5, base 15 may comprise a transport assembly 50 for (i) moving mobile CT imaging system 5 to the patient prior to scanning and (ii) moving the CT imaging system relative to the patient during scanning. More particularly, transport assembly 50 preferably comprises (i) a gross movement mechanism 55 for moving CT imaging system 5 relatively quickly across room distances, so that the CT imaging system can be quickly and easily brought to the bedside of the patient, such that the patient can be scanned at their bedside without needing to be moved to a radiology department, and (ii) a fine movement mechanism 60 for moving the CT imaging system precisely, relative to the patient, during scanning so that the patient can be scanned on their bed or gurney without needing to be moved onto a special motorized scanning table. In one preferred form of the invention, gross movement mechanism 55 preferably comprises a plurality of free-rolling casters 62, and fine movement mechanism 60 preferably comprises a plurality of centipede belt drives 63 (which can be configured for either stepped or continuous motion, whereby to provide either stepped or continuous scanning of the patient). Hydraulic apparatus 65 permits either gross movement mechanism 55 or fine movement mechanism 60 to be engaged with the floor, whereby to facilitate appropriate movement of mobile CT imaging system 5. Thus, with a mobile CT imaging system 5, the CT mobile imaging system may be pre-positioned in an "out of the way" location (e.g., in an unused corner of an emergency room) and then, when a patient requires scanning, the patient may be quickly and easily scanned at their bedside, by simply moving the mobile CT imaging system to the patient's bedside on gross movement mechanism 55 (e.g., casters 62), and thereafter moving the mobile CT imaging system during scanning on fine movement mechanism 60 (e.g., centipede belt drives 63).

Adjusting The Disposition Of The Patient Relative To The Longitudinal Axis Of The Center Opening In The Torus It has also been recognized that, in some circumstances, it can sometimes be desirable to adjust the disposition of the patient relative to the longitudinal axis of center opening 20 in torus 10.

(For the purposes of the following discussion, it can be helpful to identify the various axes associated with CT imaging system 5 and the scanning table - to this end, the "X-axis" will be considered to be the axis extending parallel to the floor, the "Y-axis" will be considered to be the axis extending perpendicular to the floor, and the "Z-axis" will be considered to be the axis extending parallel to the longitudinal axis of center opening 20 of torus 10, see FIG. 1).

More particularly, and looking now at FIGS. 6-8, a patient P is generally positioned on the scanning table T so that the longitudinal axis $A_P$ of the patient's body is aligned with the longitudinal axis $A_T$ of the scanning table, which is in turn aligned with the longitudinal axis $A_C$ of center opening 20 (FIG. 6). The patient's body is then advanced (i.e., along the Z-axis) into center opening 20, i.e., by advancing the patient support platform of scanning table T into center opening 20. However, in some cases, the longitudinal axis $A_P$ of the patient's body may not be aligned with the longitudinal axis $A_T$ of the scanning table (FIG. 7), and hence the patient may need to be repositioned on the scanning table so that they are aligned with the longitudinal axis $A_C$ of center opening 20. Or the patient may be centered on the scanning table, but the anatomy A which is to be scanned may not be aligned with the longitudinal axis $A_C$ of center opening 20 (FIG. 8), e.g., because the longitudinal axis $A_A$ of the anatomy A which is to be scanned is disposed off-center from the longitudinal axis $A_P$ of the patient's body. Because the scanning table is typically mounted to a fixed base, and comprises a patient support platform adapted to move in only the Z-direction, in both of the foregoing situations (i.e., the situations of FIGS. 7 and 8), it may be necessary to reposition the patient relative to center opening 20 of CT imaging system 5 by moving the patient on the scanning table (i.e., by moving the patient to the left or right on the patient support platform of the scanning table). However, repositioning the patient on the scanning table is not always possible or desirable. For example, if the patient is unconscious or physically handicapped or elderly, it may be difficult to reposition the patient on the scanning table. Also, the patient support platform of the scanning table is typically fairly narrow, thereby limiting the extent to which a patient may be repositioned on the scanning table.

Thus there is a need for a way to move the patient's body along the X-axis relative to the longitudinal axis of center opening 20 of torus 10 in a precise and controlled manner which does not require repositioning the patient's body on the scanning table.

Minimizing The Length Of The Motorized Scanning Table That Is Used To Scan A Patient It has also been recognized that it can be desirable to minimize the length of the motorized scanning table that is used to scan a patient using CT imaging system 5.

(Again, for the purposes of the following discussion, it can be helpful to identify the various axes associated with CT imaging system 5 and the motorized scanning table - to this end, the "X-axis" will be considered to be the axis extending parallel to the floor, the "Y-axis" will be considered to be the axis extending perpendicular to the floor, and the "Z-axis" will be considered to be the axis extending parallel to the longitudinal axis of center opening 20 of torus 10, see FIG. 1).

More particularly, motorized scanning tables are typically quite long, inasmuch as the scanning table must be long enough to accommodate the body of the patient and must be able to extend along the Z-axis for a sufficient distance to advance the anatomy into (and through) center opening 20 of CT imaging system 5. Thus, the patient support platform of the motorized scanning table is typically cantilevered a substantial distance out from the base of the motorized scanning table while the patient is being scanned.

In addition to the foregoing, it has been recognized that it is generally necessary to provide a gap between the end of the motorized scanning table and CT imaging system 5 (e.g., so as to provide room for personnel to access and service the components of CT imaging system 5 when necessary), thereby further increasing the overall length of the patient support platform of the motorized scanning table.

By way of example but not limitation, and looking now at FIGS. 9 and 10, there is shown a motorized scanning table S which comprises a fixed base F and a patient support platform L which is movable in the Z-axis relative to fixed base F, whereby to advance the anatomy which is to be scanned through the scanner. As noted above, a minimum distance M must be maintained when patient support platform L of motorized scanning table S is in its fully retracted configuration, and patient support platform L must be long enough to advance all of the anatomy which is to be scanned through the scanner. Thus, patient support platform L must be long enough to accommodate the length of the patient and to advance the length of the patient over the distance M and the distance B in order to permit complete scanning of the patient.

For these reasons, patient support platform L of motorized scanning table S must typically be quite long, and it must cantilever a substantial distance out from fixed base F of motorized scanning table S. However, it is also very important that motorized scanning table S provide a stable support for the patient, even when patient support platform L is cantilevered out a significant distance away from fixed base F of motorized scanning table S, in order to permit proper imaging of the patient. And this must be accomplished even when dealing with heavy-set patients who impose a substantial load on the cantilevered patient support platform L.

In practice, several different types of motorized scanning tables exist.

One type of motorized scanning table is the motorized scanning table S shown in FIGS. 9 and 10, which utilize a fixed base F and a patient support platform L that can move along the Z-axis relative to fixed base F. However, with this type of motorized scanning table, because fixed base F does not move along the Y-axis (i.e., up and down), it can be challenging for some patients (e.g., elderly patients, obese patients, etc.) to get on or off the motorized scanning table.

To address this problem, and looking now at FIGS. 11 and 12, most motorized scanning tables utilize a so-called "scissor" lift mechanism to raise and lower patient support platform L. More particularly, in this form of motorized scanning table, motorized scanning table S comprises fixed base F, a table top N and patient support platform L. A "scissor" lift mechanism Q is used to move table top N along the Y-axis relative to fixed base F, and a transport mechanism (not shown) is used to move patient support platform L along the Z-axis relative to table top N. Scissor lift mechanism Q generally comprises two scissor pairs, one on each side of fixed base F, where each scissor pair itself comprises a pair of crossed arms, with one end of each arm being pivotally connected to either fixed base F or table top N, and with the other end of each arm being slidably connected to the other of fixed base F or table top N, and with the pair of crossed arms being pivotally connected to each other intermediate their length (FIG. 11). By virtue of this construction, table top N of scanning table S can move along the Y-axis relative to fixed base F so as to permit the motorized scanning table to be raised and lowered, e.g., table top N of motorized scanning table S can be lowered to help a patient get onto the patient support platform L of the motorized scanning table, and then table top N of motorized scanning table S can be raised so that the patient is at the proper level for scanning. During scanning, patient support platform L can be moved along the Z-axis relative to table top N for advancing the patient into center opening 20 of CT imaging system 5. p Note that with the "scissor lift" motorized scanning table S of FIGS. 11 and 12, the distance that patient support platform L must be cantilevered out over fixed base F of the motorized scanning table remains the same as with the fixed-height motorized scanning table of FIGS. 9 and 10, regardless of the position of table top N along the Y-axis.

However, as noted above, because patient support platform L of motorized scanning table S is cantilevered out over fixed base F of motorized scanning table S and must support significant weight (i.e., the weight of the patient disposed on the cantilevered patient support platform L), it has been recognized that it is desirable to minimize the distance which patient support platform L must be cantilevered out over fixed base F of the motorized scanning table during scanning.

To this end, another type of scanning table (sometimes referred to as the so-called "cobra" style motorized scanning table) has been developed. More particularly, and looking now at FIGS. 13 and 14, with the "cobra" style motorized scanning table, motorized scanning table S still comprises fixed base F, table top N and patient support platform L. However, with the "cobra" style scanning table, a pair of parallel arms are pivotally mounted to fixed base F of motorized scanning table S and pivotally mounted to table top N, thereby enabling table top N to move through an arc about fixed base F of motorized scanning table S (FIG. 14), whereby to simultaneously move table top N along both the Y-axis and the Z-axis. Because table top N moves along the Y-axis (e.g., by the distance C shown in FIG. 14), the overall length of patient support platform L can be reduced by the distance C, thereby reducing the distance that patient support platform L must be cantilevered out over fixed base F. Unfortunately, however, the "cobra" style scanning table lacks stability because its parallel arms do not reinforce one another (unlike the "scissor lift" style motorized table of FIGS. 11 and 12, where the crossed arms of the scissor lift mechanism are connected together intermediate their length and thereby reinforce each other).

Thus there is a need for a new and improved motorized scanning table which is configured to move along the Y-axis (i.e., up and down) while also moving along the Z-axis, whereby to reduce the distance that the patient support platform must be cantilevered out over the fixed base of the motorized scanning table, while providing increased stability.

SUMMARY OF THE INVENTION

These and other objects of the present invention are addressed by the provision and use of a novel scanning table, wherein the portion of the table which supports the patient can be moved along the X-axis, whereby to move the patient's body relative to the longitudinal axis of center opening 20 in a precise and controlled manner which does not require repositioning the patient's body on the scanning table.

Thus the present invention provides a novel scanning table which allows a patient that is positioned off-center of the longitudinal axis of the scanning table to be moved along the X-axis so as to align the patient with the longitudinal axis of center opening 20 (FIG. 15). The present invention also allows a patient to be moved along the X-axis so as to align particular anatomy with the longitudinal axis of center opening 20 (FIG. 16).

The present invention also comprises the provision and use of a new and improved motorized scanning table which is configured to move along the Y-axis (i.e., up and down) while also moving along the Z-axis, whereby to reduce the distance that the patient support platform must be cantilevered out over the fixed base of the motorized scanning table, while providing increased stability.

In one preferred form of the invention, there is provided a novel scanning table for use with a scanning machine, the novel scanning table comprising:
a fixed base;
a movable table top movably mounted to the fixed base for permitting the movable table top to be moved along the X-axis relative to the fixed base; and
a movable patient support platform movably mounted to the movable table top for permitting the movable patient support platform to be moved along the Z-axis relative to the movable table top.

In another preferred form of the invention, there is provided a system comprising:
an imaging system; and
a scanning table comprising:
a fixed base;
a movable table top movably mounted to the fixed base for permitting the movable table top to be moved along the X-axis relative to the fixed base; and
a movable patient support platform movably mounted to the movable table top for permitting the movable patient support platform to be moved along the Z-axis relative to the movable table top.

In another preferred form of the invention, there is provided a method for scanning a patient, the method comprising:

providing an imaging system and providing a scanning table, the scanning table comprising:
a fixed base;
a movable table top movably mounted to the fixed base for permitting the movable table top to be moved along the X-axis relative to the fixed base; and
a movable patient support platform movably mounted to the movable table top for permitting the movable patient support platform to be moved along the Z-axis relative to the movable table top;
positioning the patient on the movable patient support platform;
moving the movable table top relative to the fixed base so as to adjust the disposition of the patient relative to the imaging system; and
moving the movable patient support platform while using the imaging system to scan the patient.

In another preferred form of the invention, there is provided a novel motorized scanning table for use with a scanning machine, the novel motorized scanning table comprising:
a fixed base;
a movable table top movably mounted to the fixed base for permitting the movable table top to be simultaneously moved along the Y-axis and the Z-axis relative to the fixed base, wherein the movable table top is movably mounted to the fixed base by a scissor mount comprising two scissor pairs, each scissor pair comprising a pair of support arms connected to one another intermediate their length by a pivot mount, and further wherein one support arm from each pair of support arms is slidably mounted to the fixed base at one end of the support arm and is slidably mounted to the movable table top at the other end of the support arm, and the other support arm from each pair of support arms is pivotally mounted to the fixed base at one end of the support arm and is pivotally mounted to the movable table top at the other end of the support arm; and
a movable patient support platform movably mounted to the movable table top for permitting the movable patient support platform to be moved along the Z-axis relative to the movable table top.

In another preferred form of the invention, there is provided a system comprising:
an imaging system; and
a motorized scanning table comprising:
a fixed base;
a movable table top movably mounted to the fixed base for permitting the movable table top to be simultaneously moved along the Y-axis and the Z-axis relative to the fixed base, wherein the movable table top is movably mounted to the fixed base by a scissor mount comprising two scissor pairs, each scissor pair comprising a pair of support arms connected to one another intermediate their length by a pivot mount, and further wherein one support arm from each pair of support arms is slidably mounted to the fixed base at one end of the support arm and is slidably mounted to the movable table top at the other end of the support arm, and the other support arm from each pair of support arms is pivotally mounted to the fixed base at one end of the support arm and is pivotally mounted to the movable table top at the other end of the support arm; and
a movable patient support platform movably mounted to the movable table top for permitting the movable patient support platform to be moved along the Z-axis relative to the movable table top.

In another preferred form of the invention, there is provided a method for scanning a patient, the method comprising:

providing an imaging system and providing a motorized scanning table, the motorized scanning table comprising:
a fixed base;
a movable table top movably mounted to the fixed base for permitting the movable table top to be simultaneously moved along the Y-axis and the Z-axis relative to the fixed base, wherein the movable table top is movably mounted to the fixed base by a scissor mount comprising two scissor pairs, each scissor pair comprising a pair of support arms connected to one another intermediate their length by a pivot mount, and further wherein one support arm from each pair of support arms is slidably mounted to the fixed base at one end of the support arm and is slidably mounted to the movable table top at the other end of the support arm, and the other support arm from each pair of support arms is pivotally mounted to the fixed base at one end of the support arm and is pivotally mounted to the movable table top at the other end of the support arm; and
a movable patient support platform movably mounted to the movable table top for permitting the movable patient support platform to be moved along the Z-axis relative to the movable table top;
positioning the patient on the movable patient support platform;
moving the movable table top relative to the fixed base so as to adjust the disposition of the patient relative to the imaging system; and
moving the movable patient support platform while using the imaging system to scan the patient.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE
PREFERRED EMBODIMENTS

Adjusting The Disposition Of The Patient Relative
To The Longitudinal Axis Of The Center Opening
In The Torus In accordance with the present invention, there is provided a novel scanning table, wherein the portion of the table which supports the patient can be moved along the X-axis, whereby to move the patient's body relative to the longitudinal axis of center opening 20 in a precise and controlled manner which does not require repositioning the patient's body on the scanning table.

Figure 1:
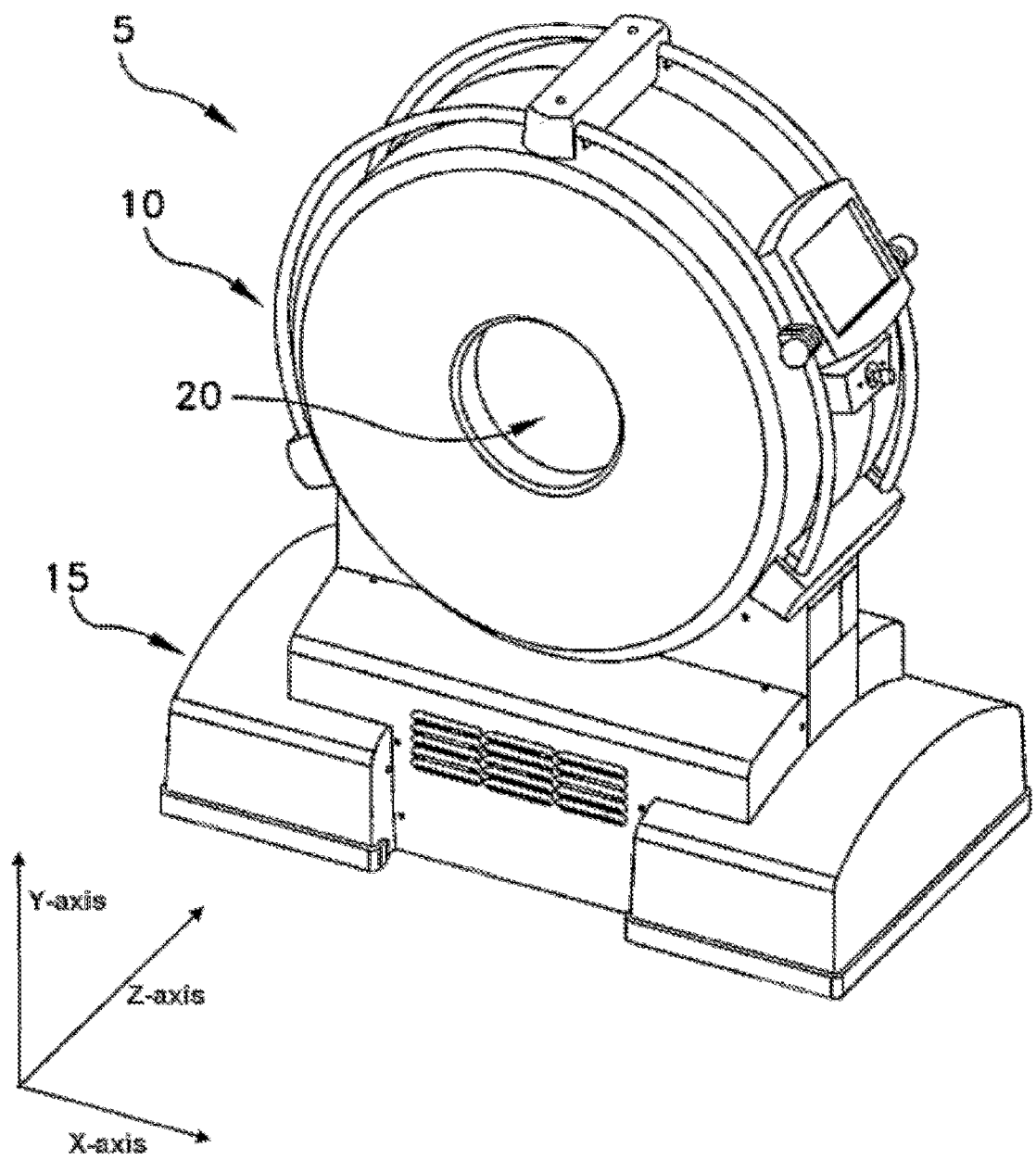
FIGS. 1 and 2 are schematic views showing the exterior of an exemplary CT imaging system.
Figure 2:
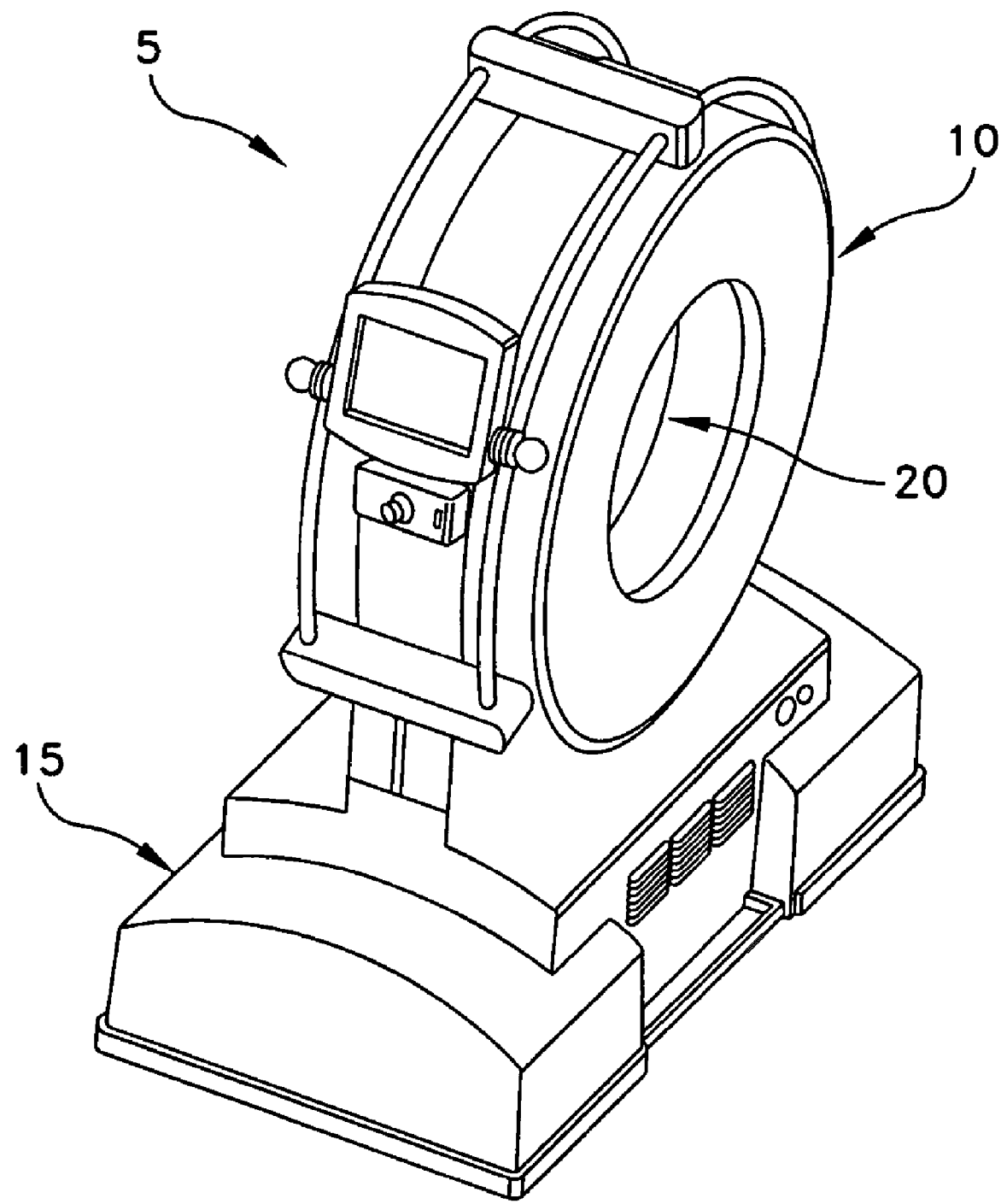
Figure 3:
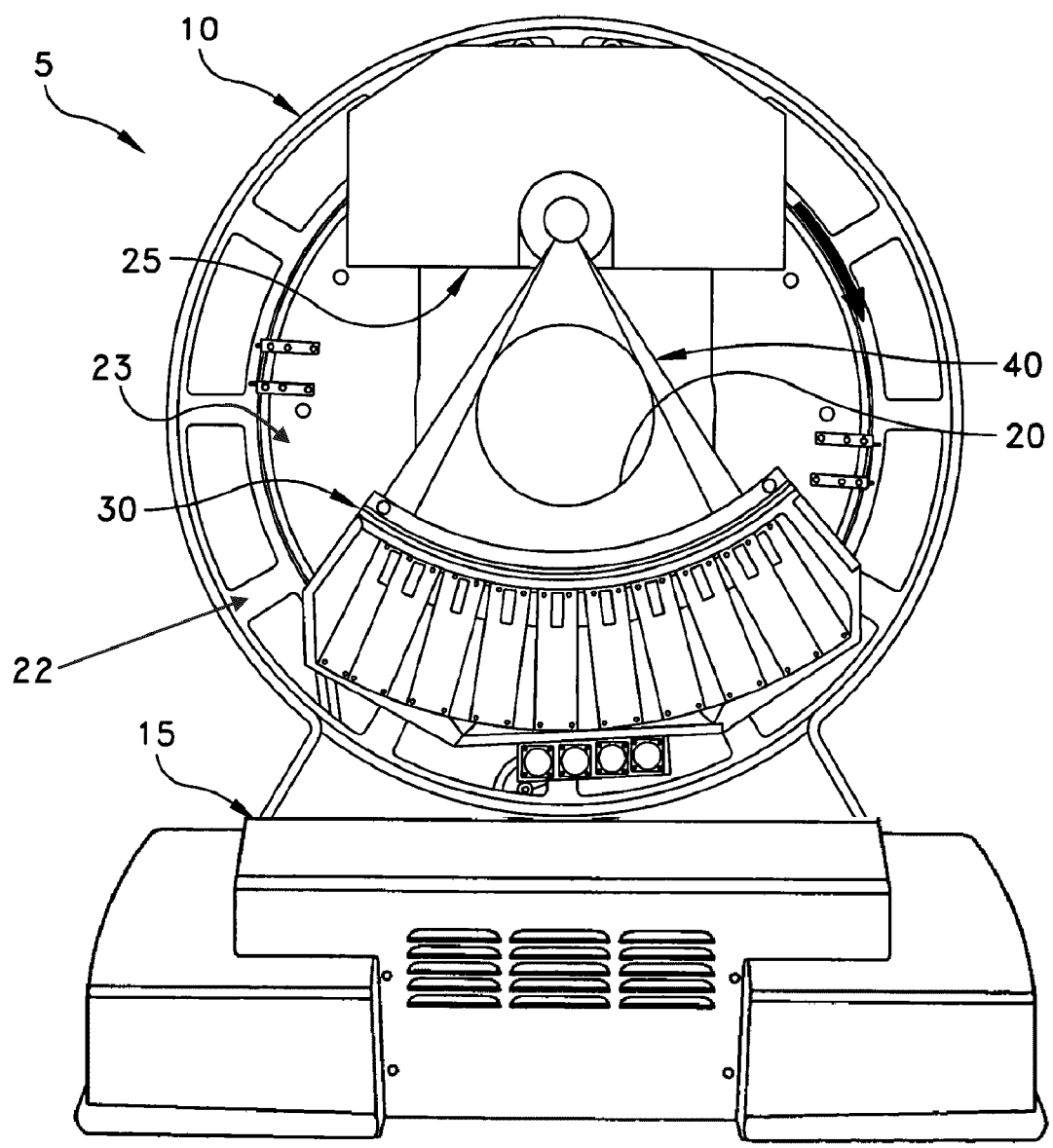
FIG. 3 is a schematic view showing various components in the torus of the exemplary CT imaging system shown in FIGS. 1 and 2.
Figure 4:
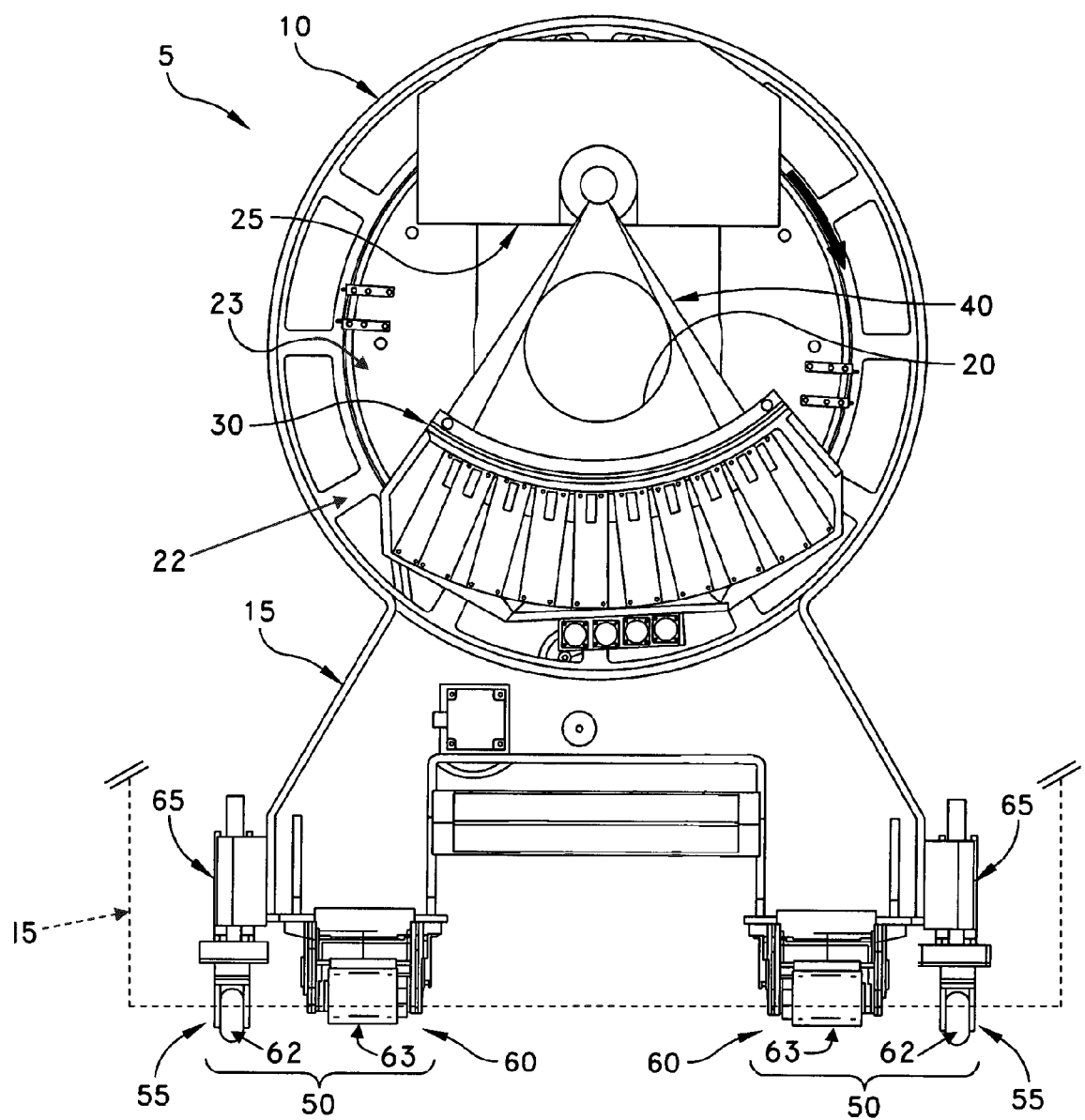
FIGS. 4 and 5 are schematic views showing an exemplary transport assembly for an exemplary CT imaging system.
Figure 5:
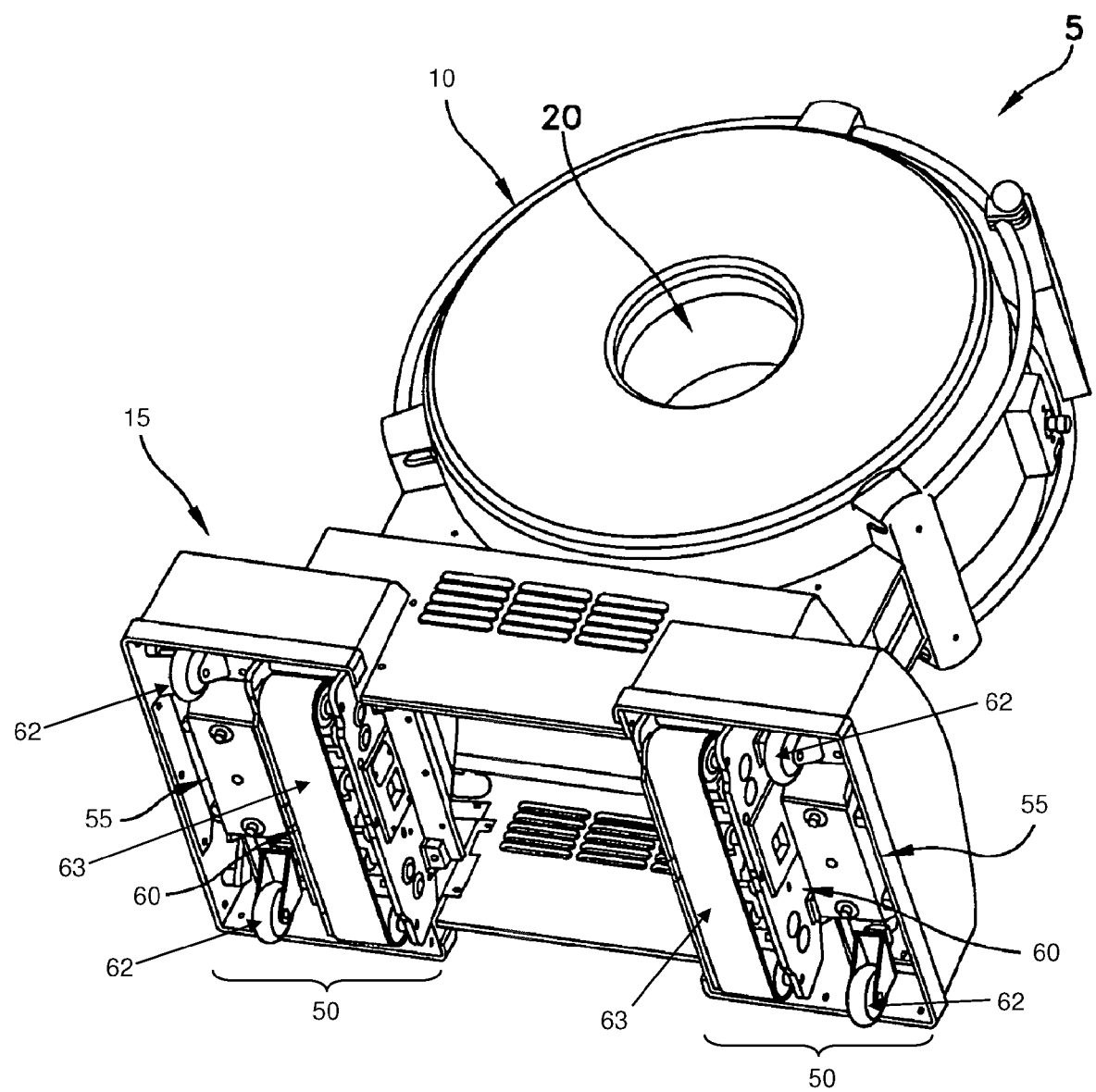
Figure 6:
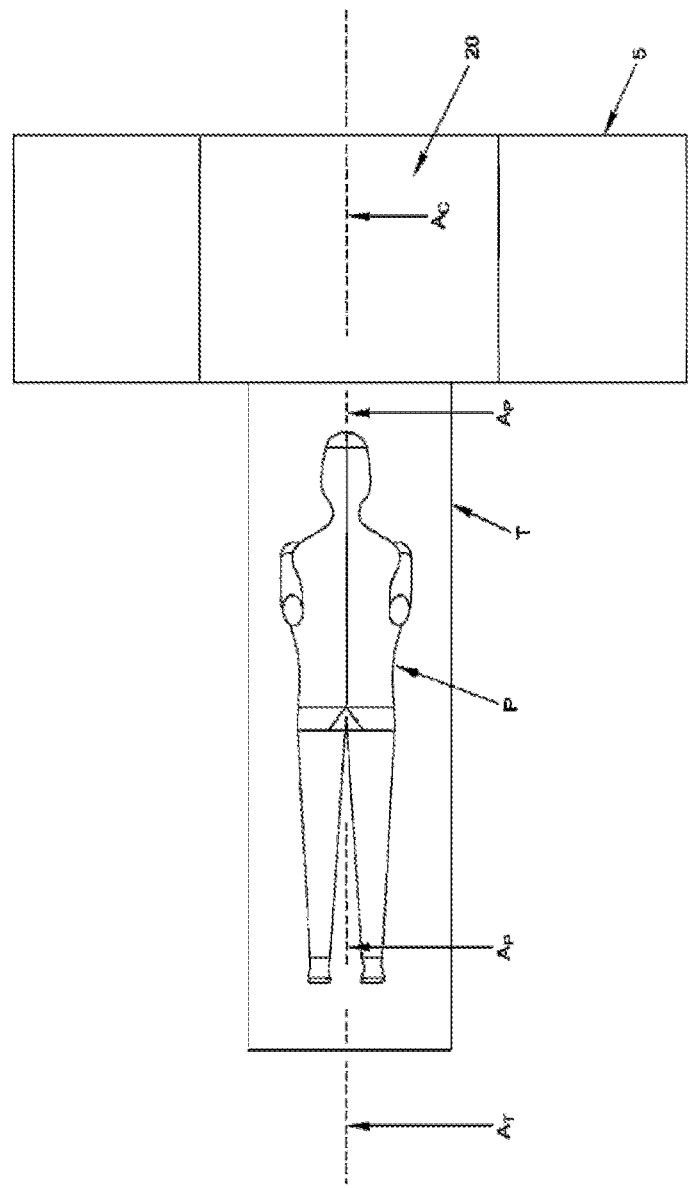
FIG. 6 is a schematic view showing how a patient centered on a scanning table will be aligned with the longitudinal axis of the CT imaging system.
Figure 7:
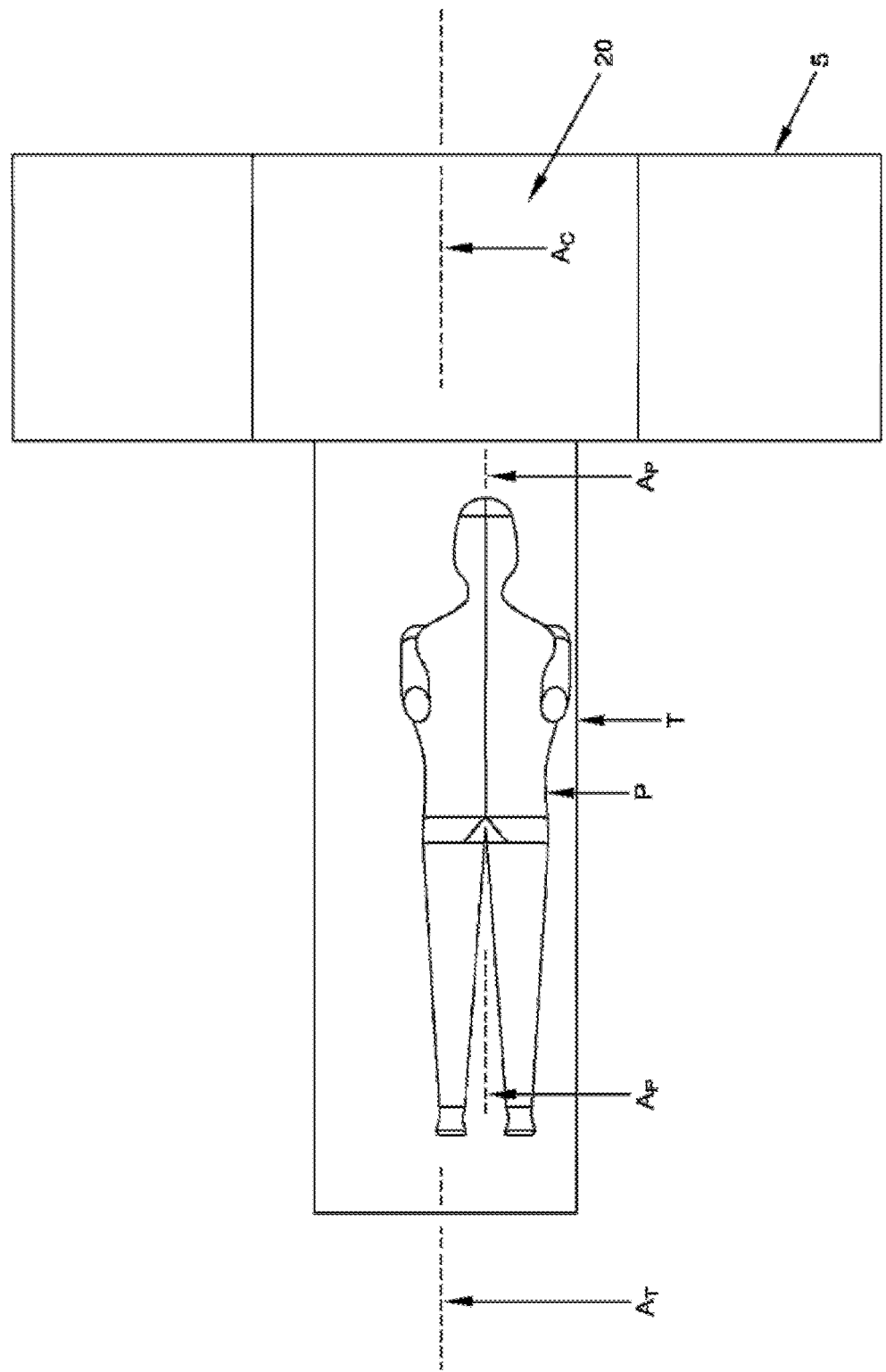
FIG. 7 is a schematic view showing how a patient not centered on the scanning table will not be aligned with the longitudinal axis of the CT imaging system.
Figure 8:
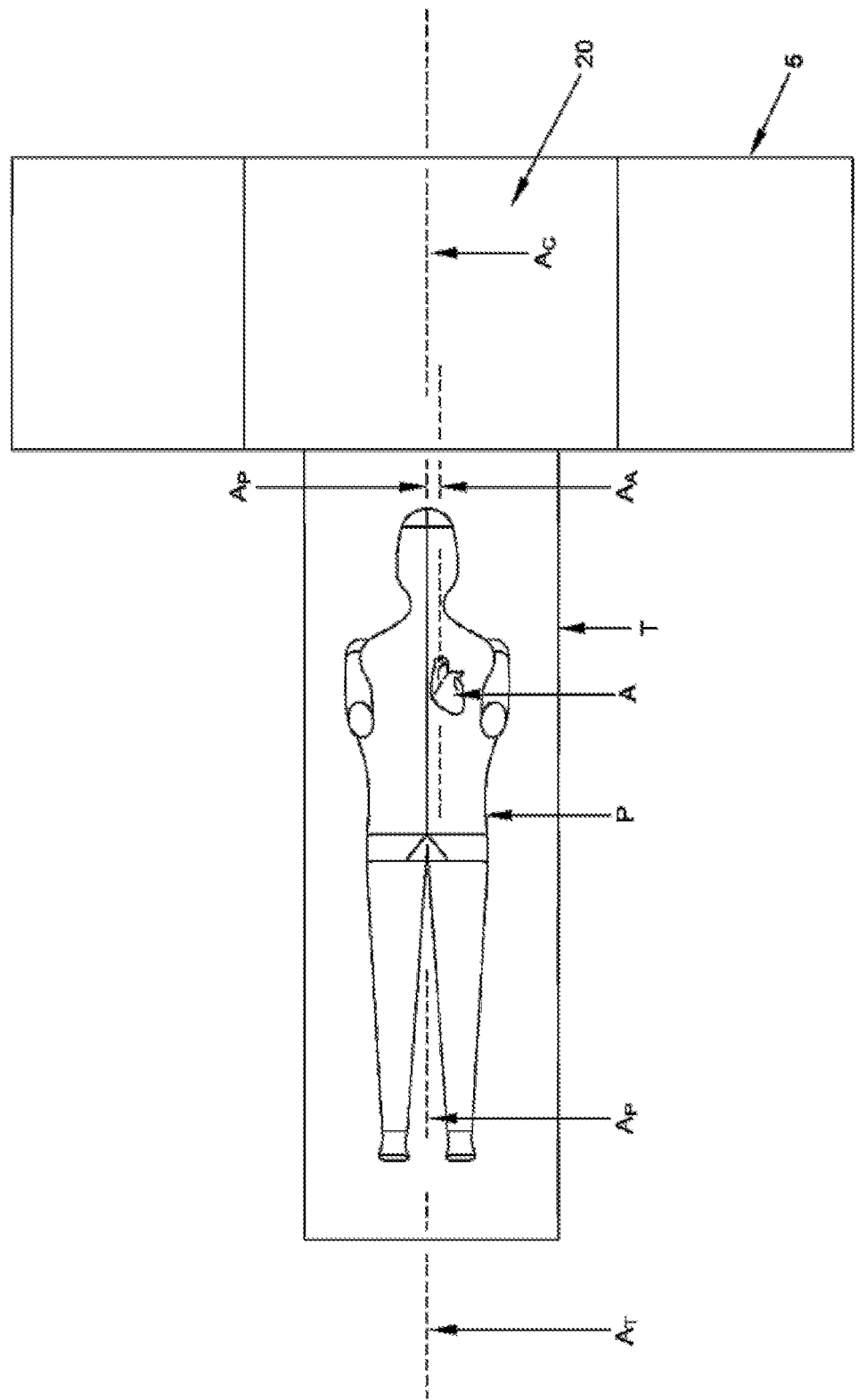
FIG. 8 is a schematic view showing that even when a patient may be centered on the scanning table, anatomy of interest may not be aligned with the longitudinal axis of the CT imaging system.
Figure 9:
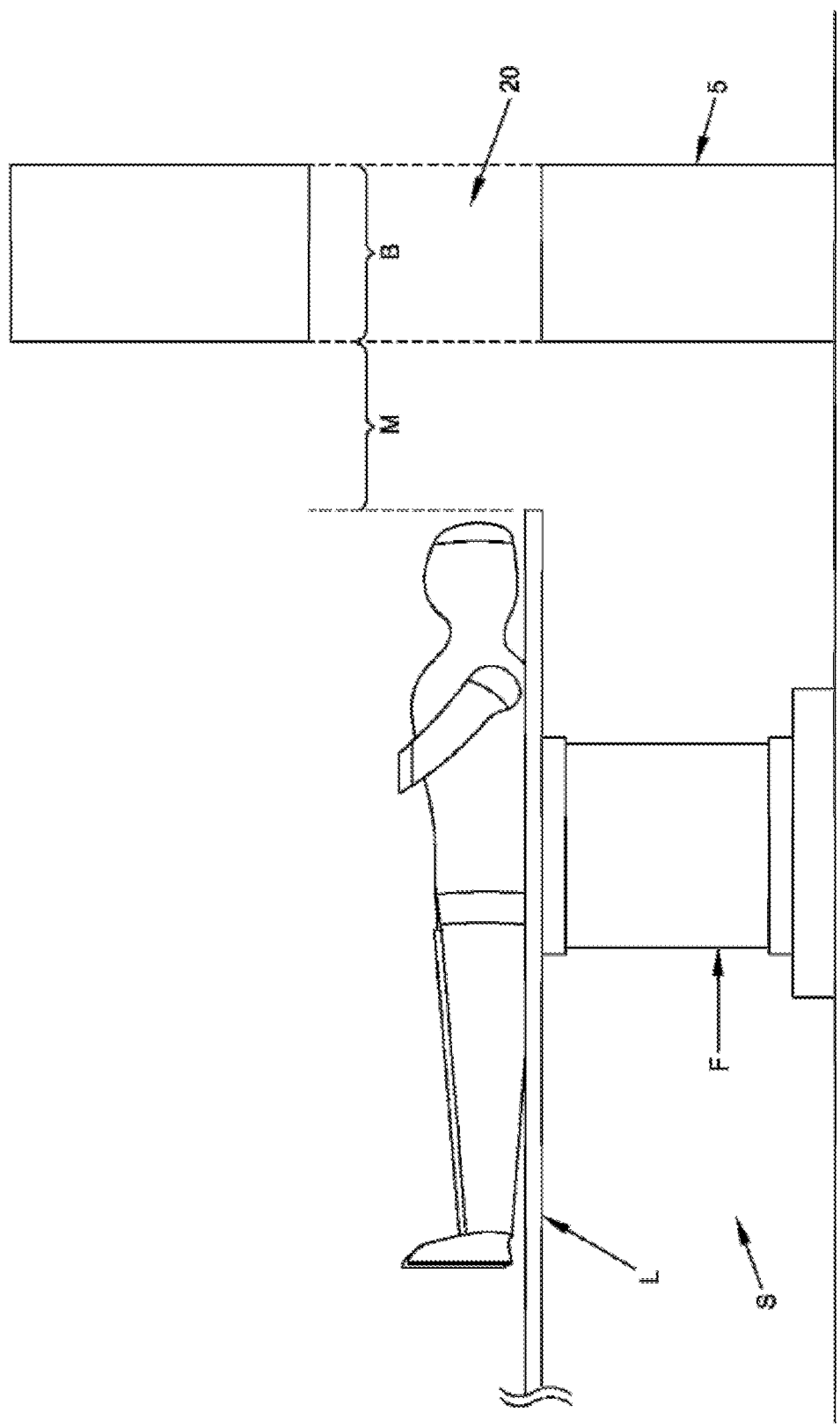
FIGS. 9-14 are schematic views illustrating several exemplary prior art motorized scanning tables.
Figure 10:
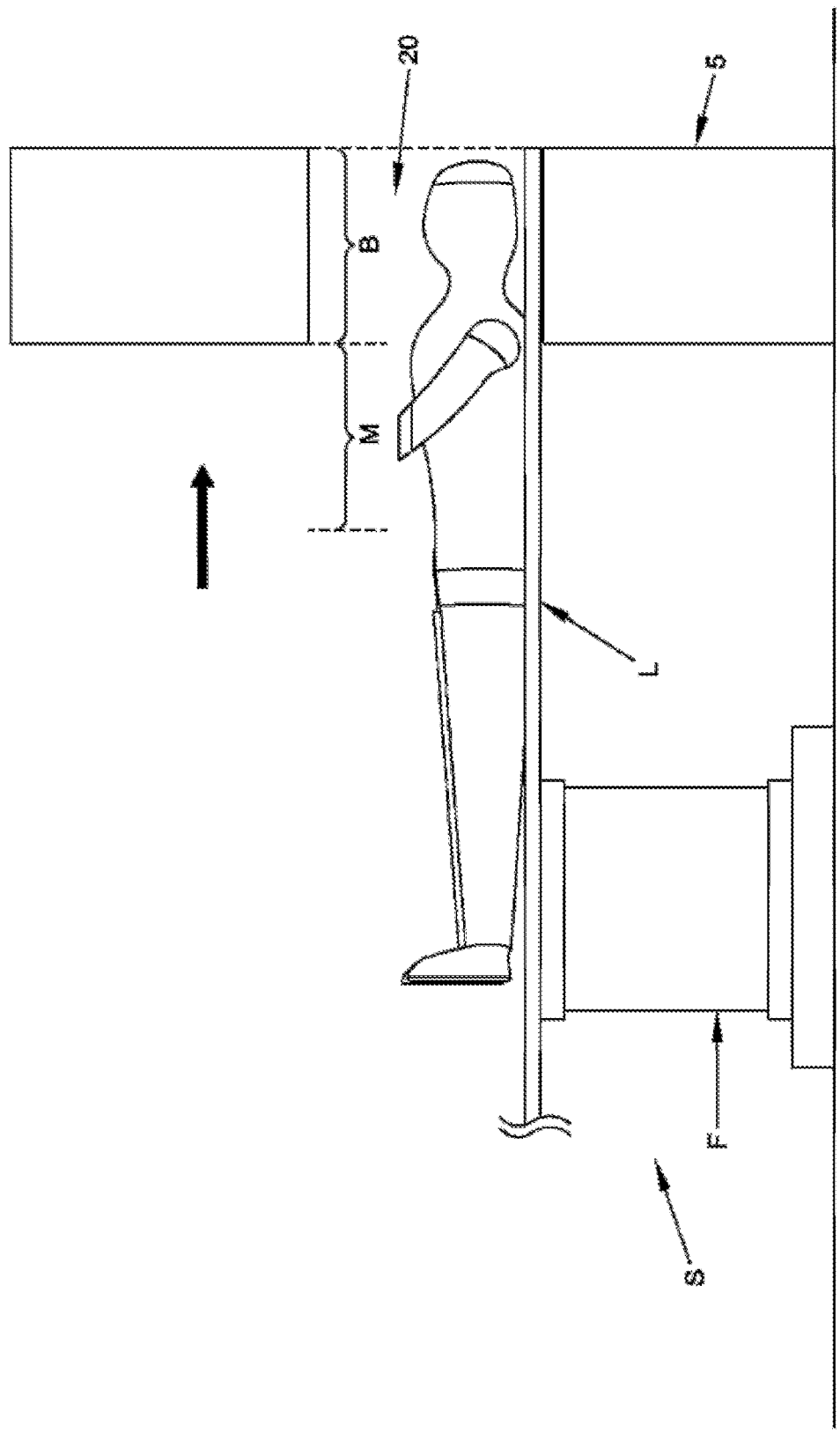
Figure 11:
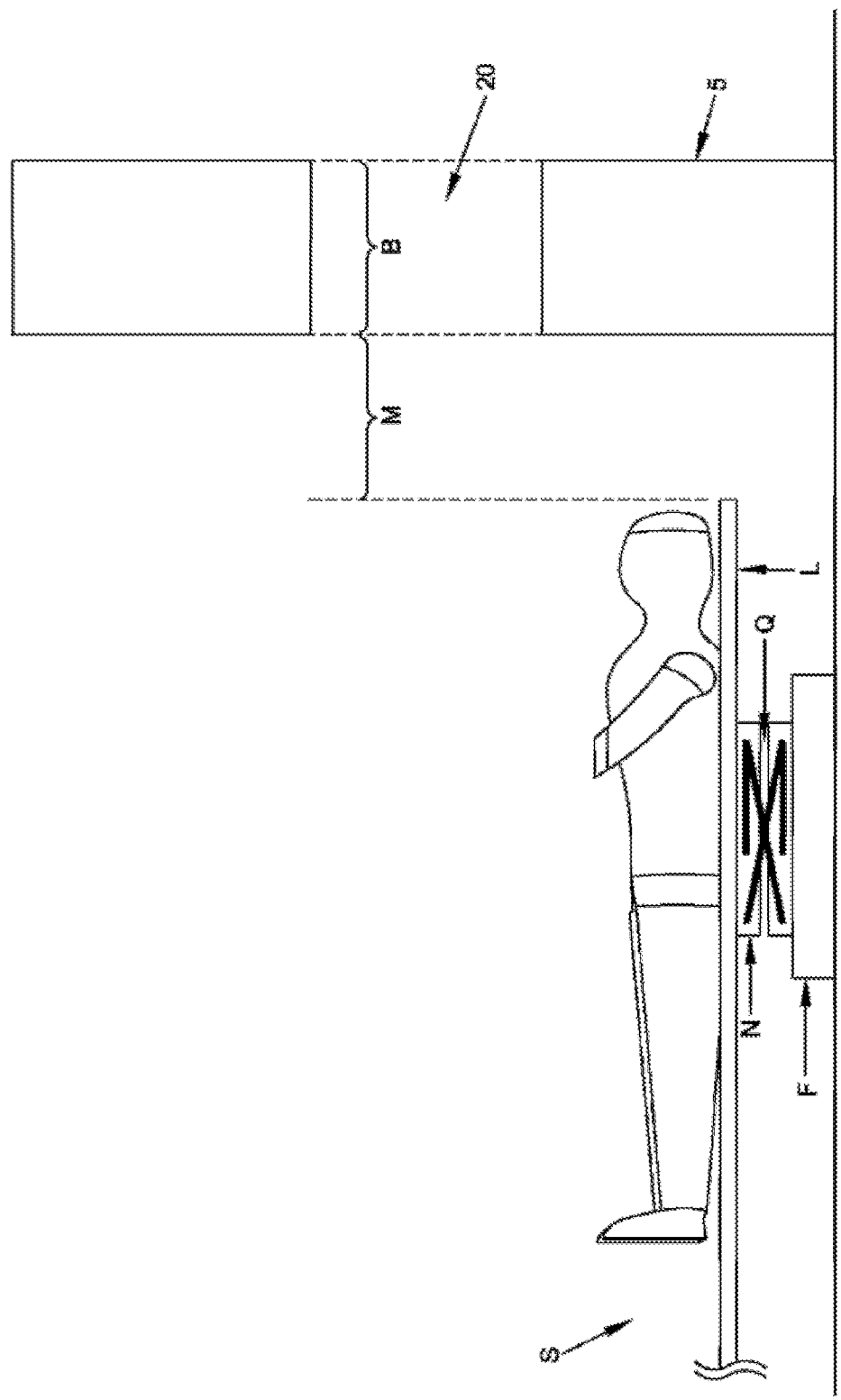
Figure 12:
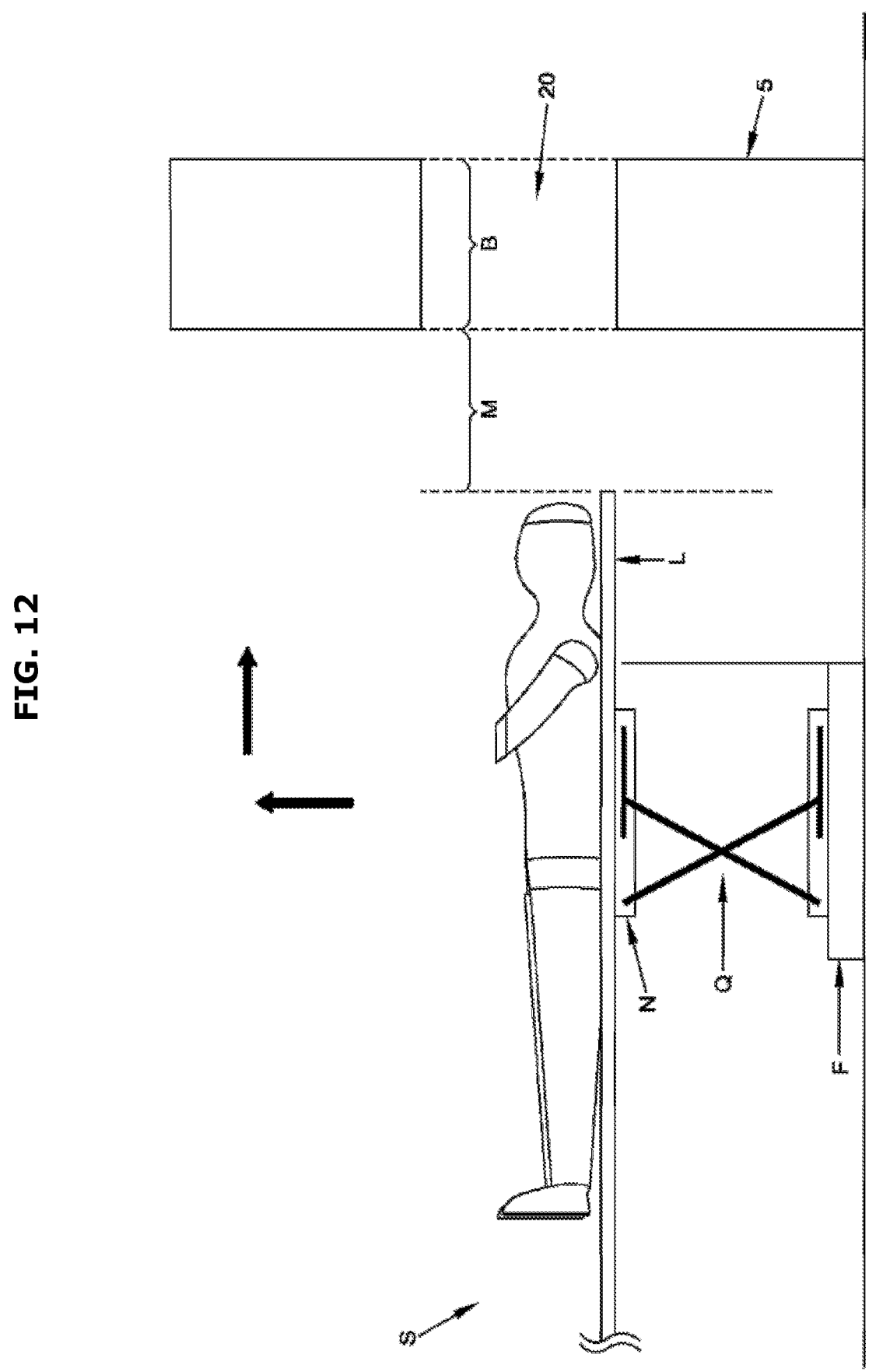
Figure 13:
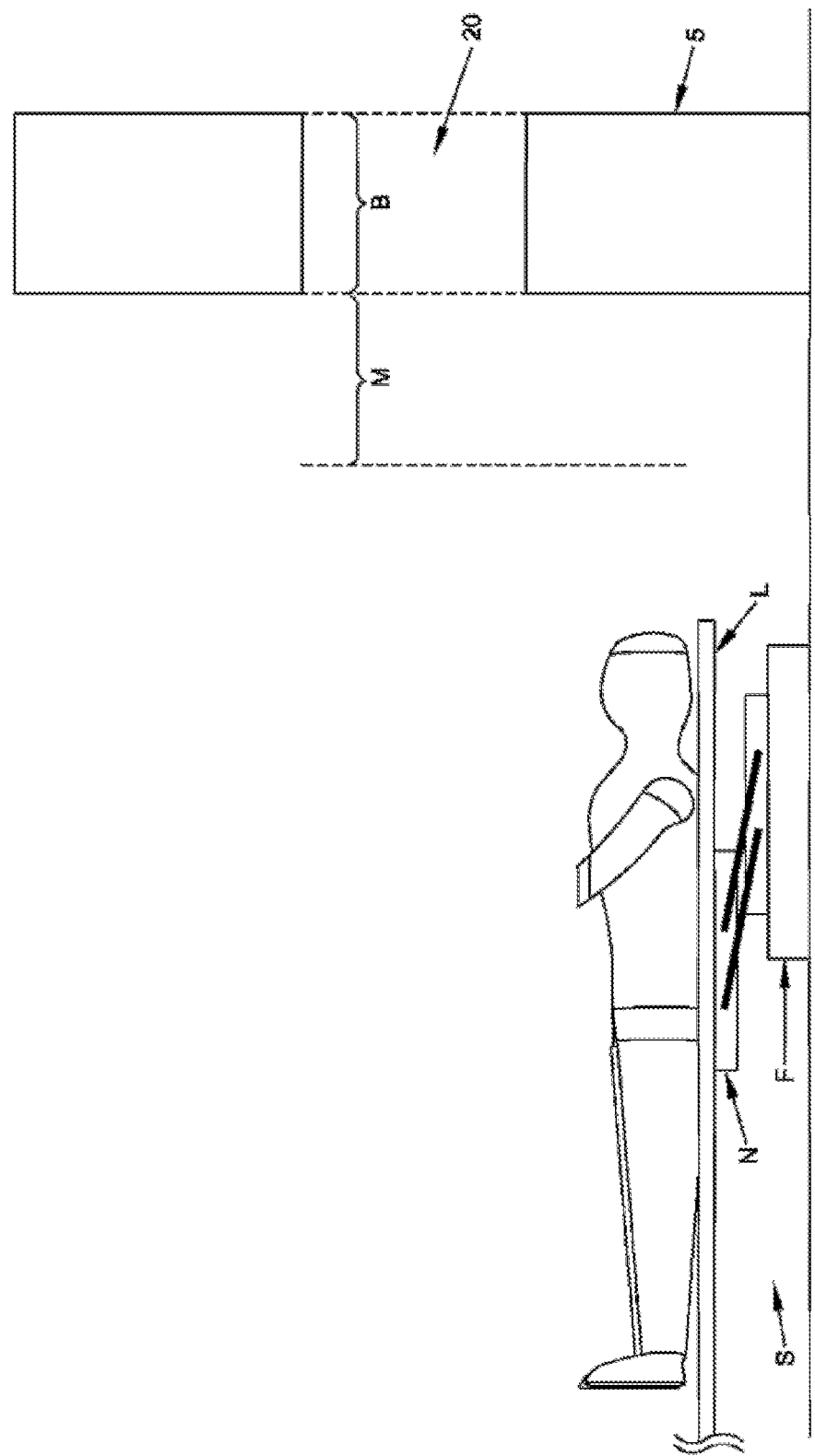
Figure 14:
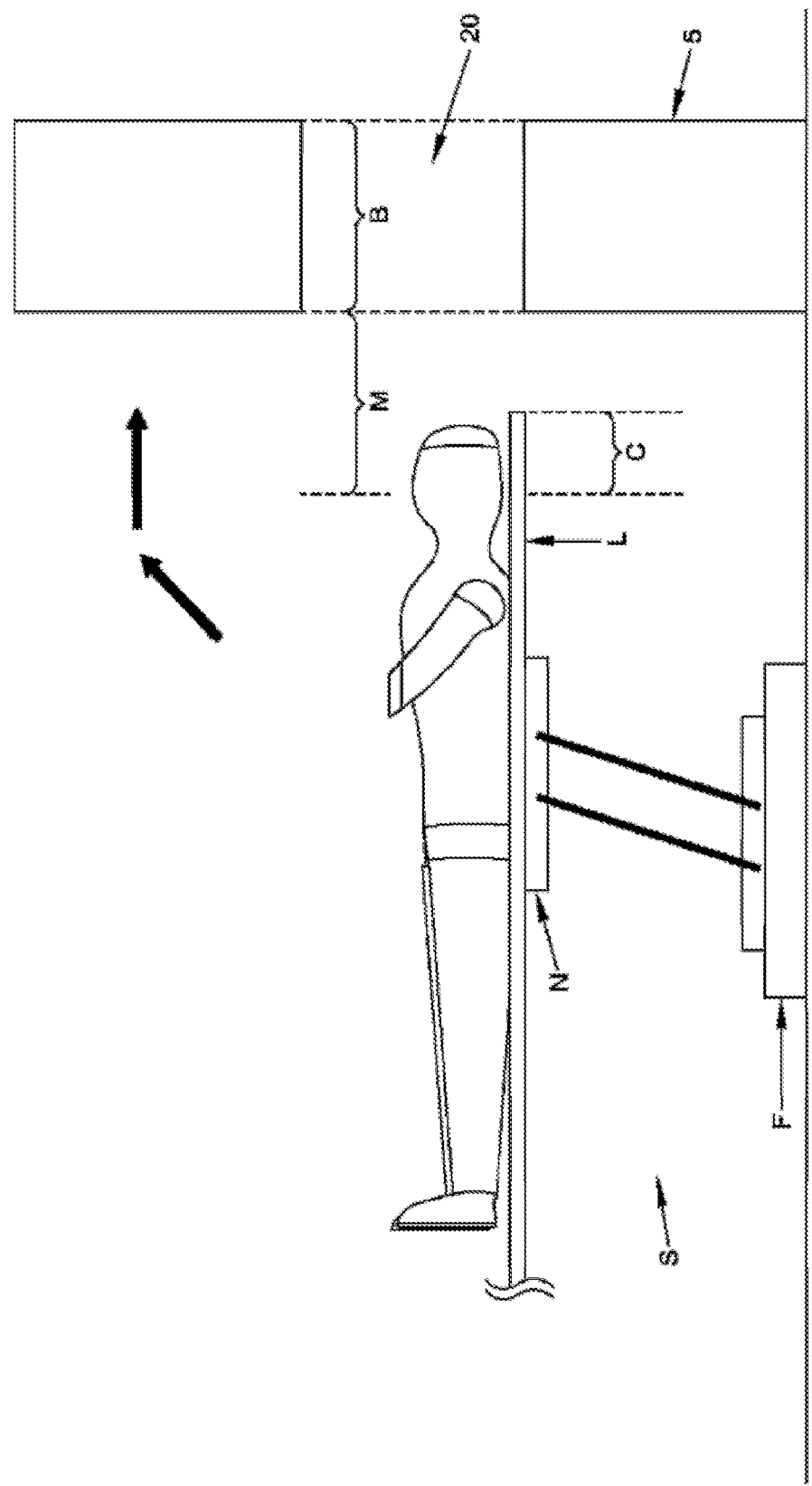
Figure 15:
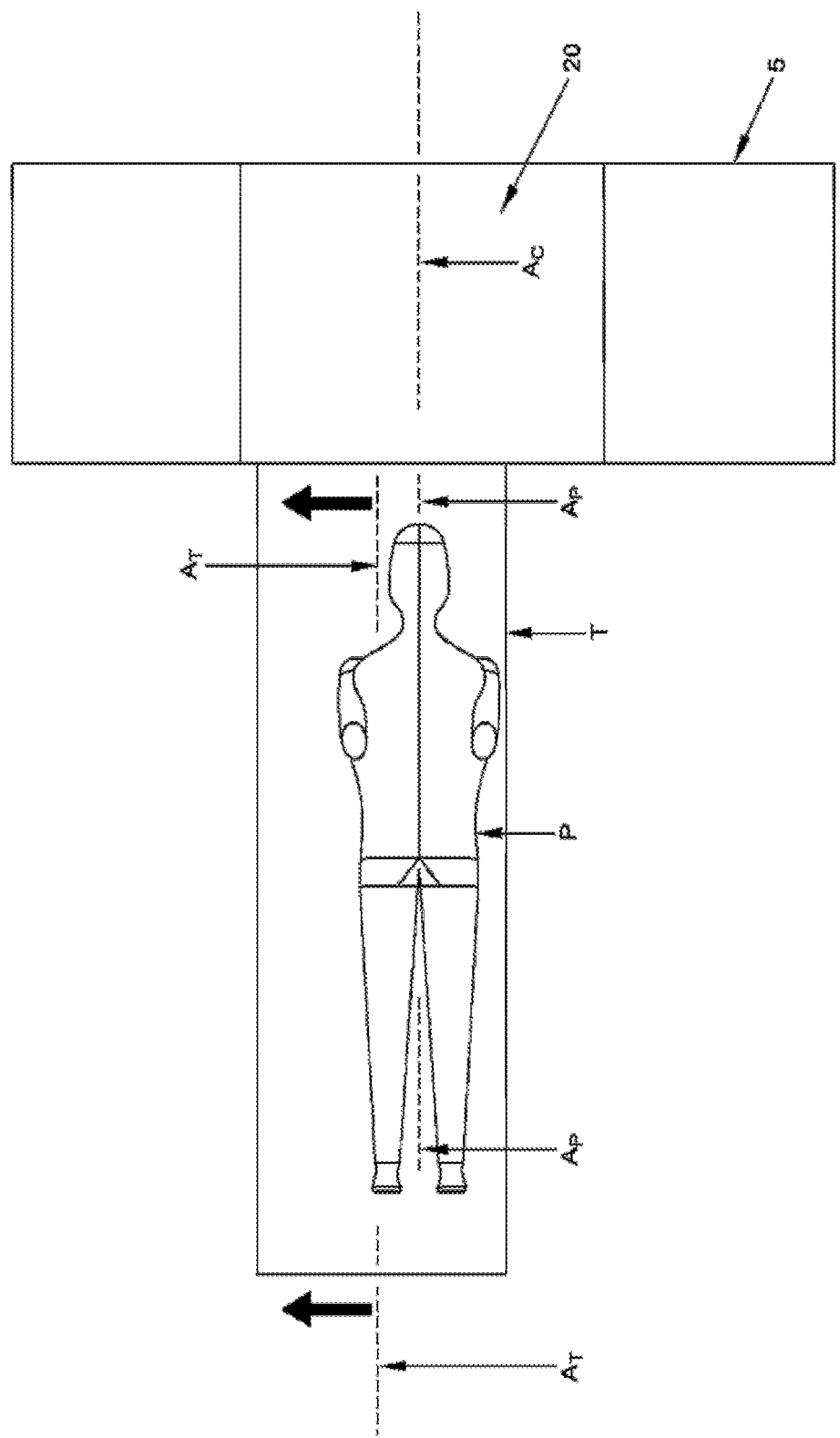
FIGS. 15 and 16 are schematic views illustrating how a patient and/or anatomy may be aligned with the longitudinal axis of the CT imaging system by moving the scanning table along the X-axis.
Figure 16:
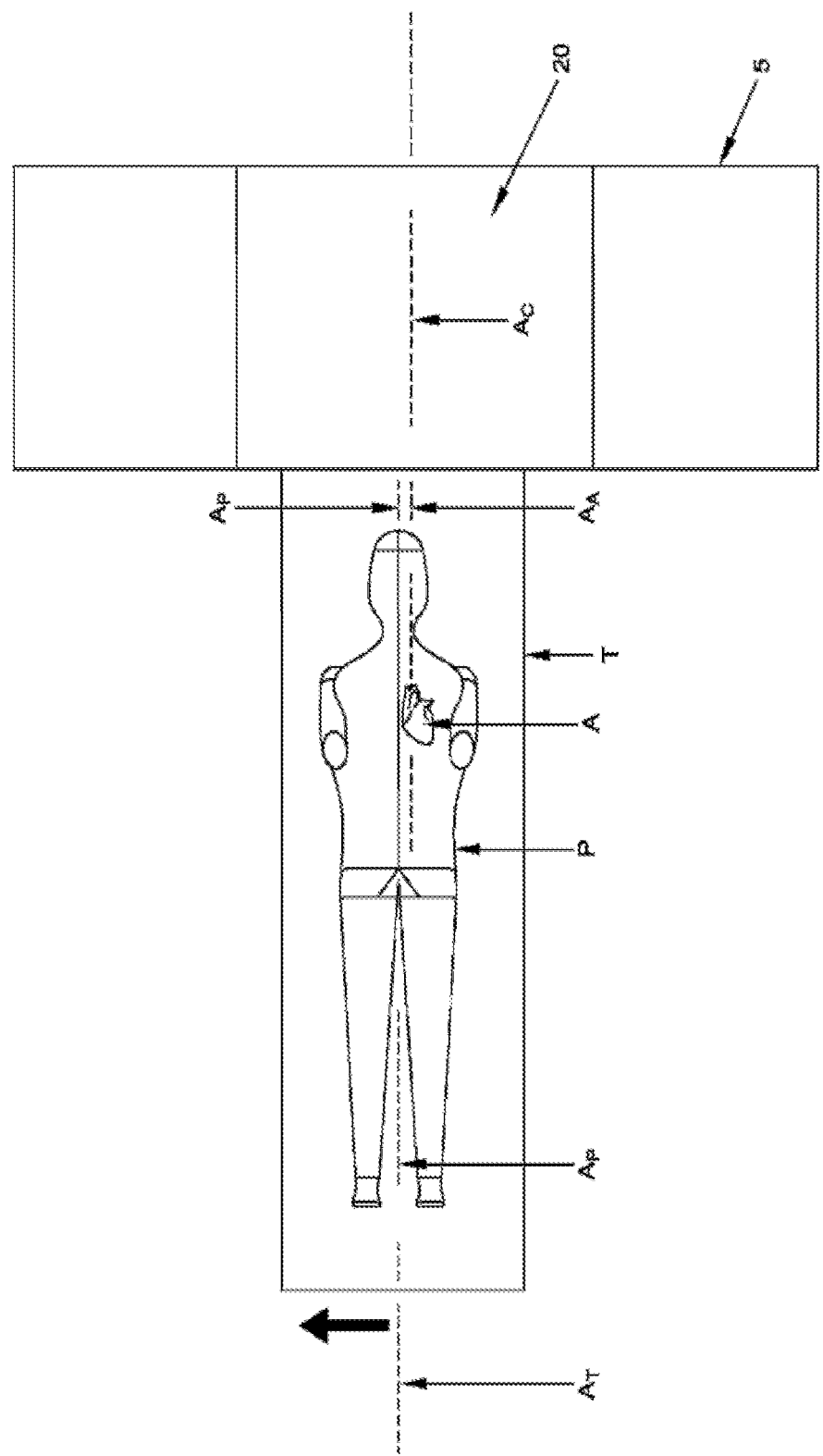

Thus the present invention provides a novel scanning table which allows a patient that is positioned off-center of the longitudinal axis of the scanning table to be moved along the X-axis so as to align the patient with the longitudinal axis of center opening 20 (FIG. 15). The present invention also allows a patient to be moved along the X-axis so as to align particular anatomy with the longitudinal axis of center opening 20 (FIG. 16).

Figure 17:
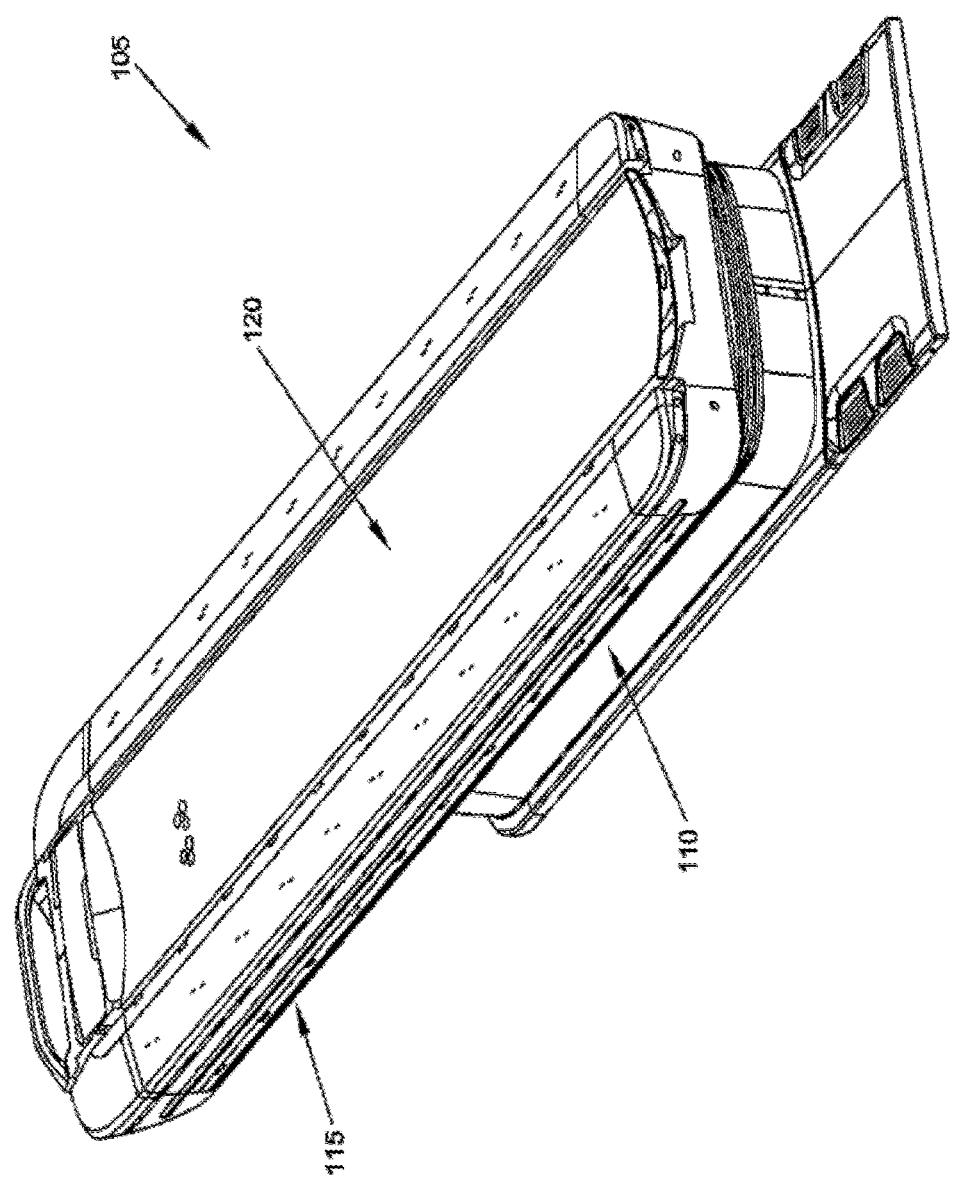
FIGS. 17-19 are schematic views showing a novel scanning table formed in accordance with the present invention, wherein the novel scanning table comprises a table top which is movable along the X-axis.
Figure 18:
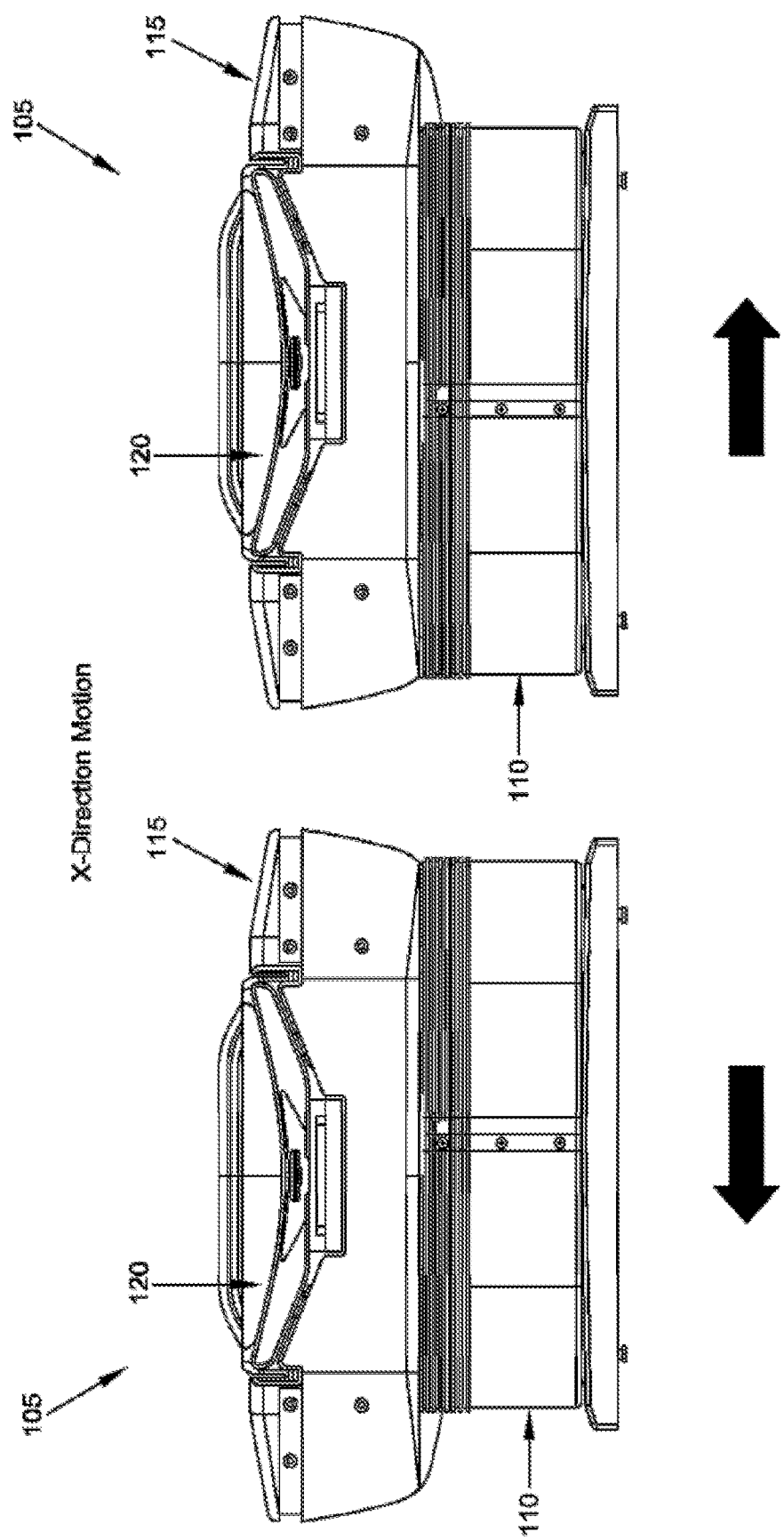
Figure 19:
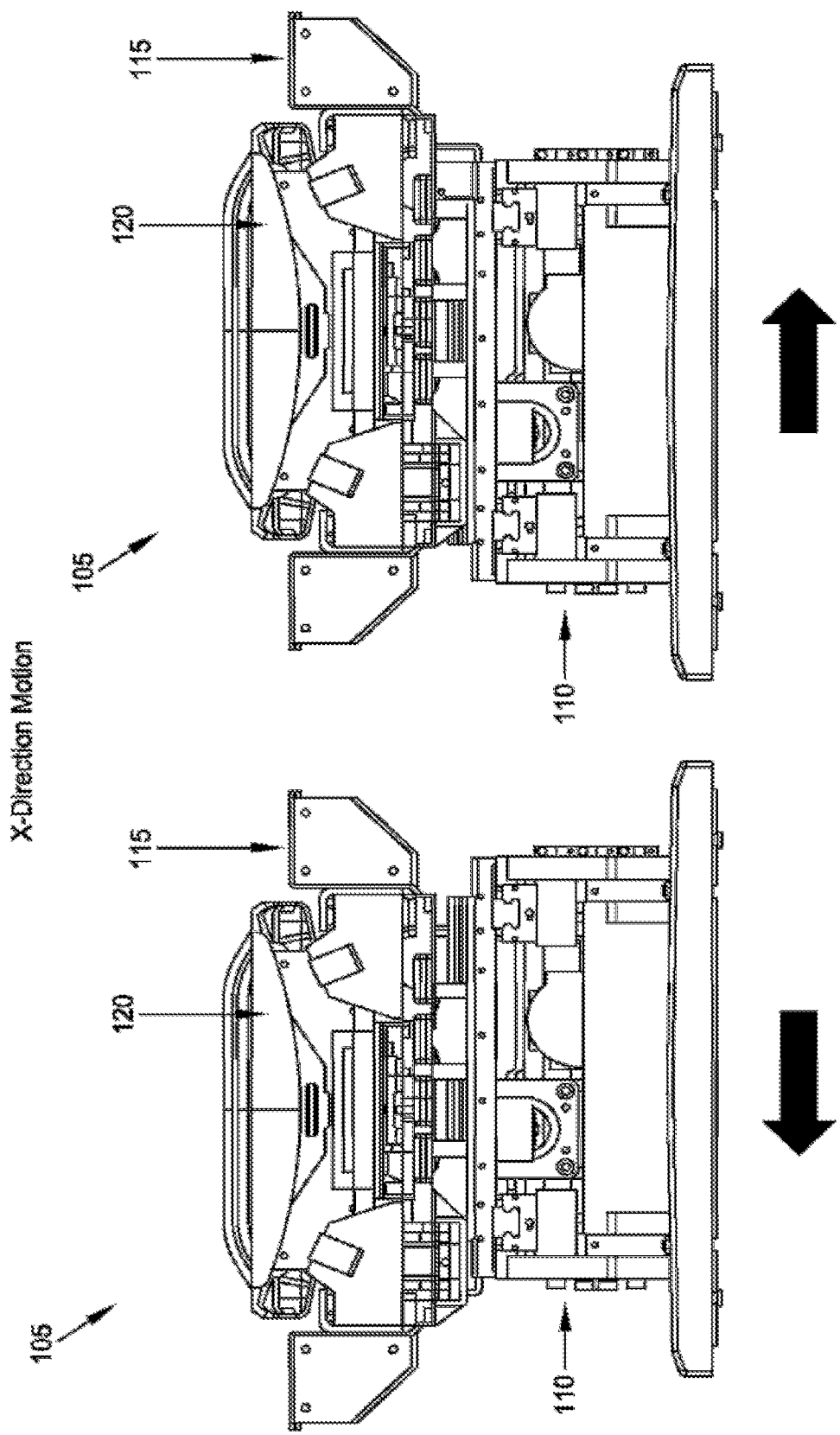
Figure 20:
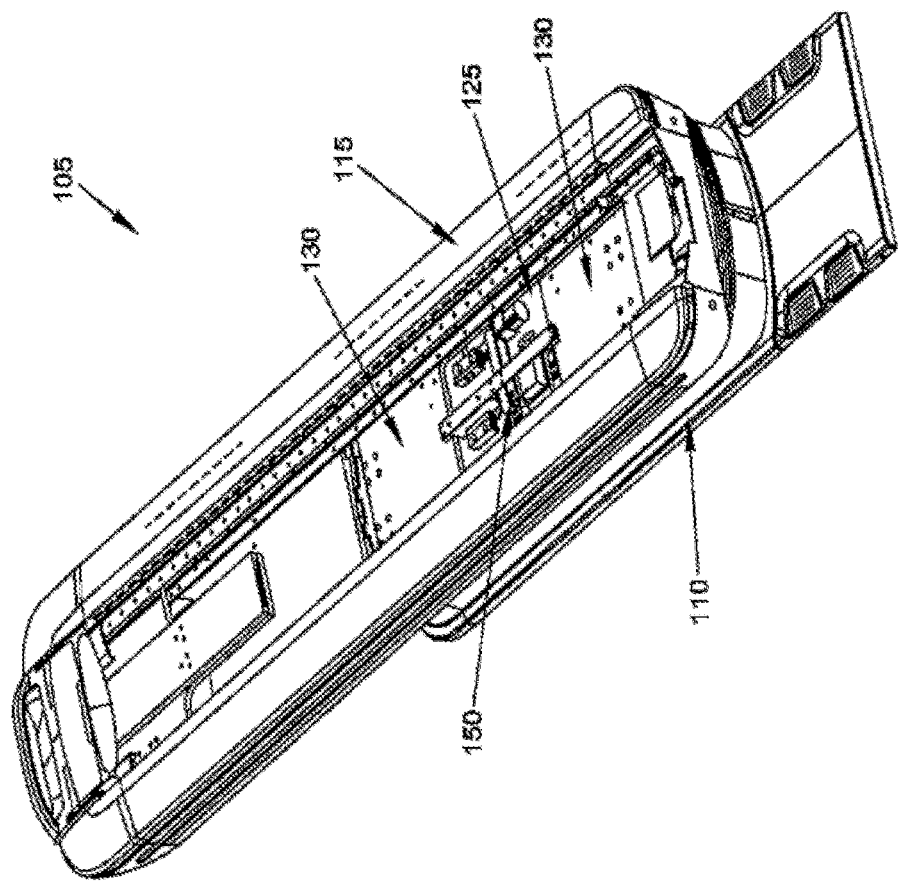
FIGS. 20-26 are schematic views showing construction details of the novel scanning table of FIGS. 17-19.
Figure 21:
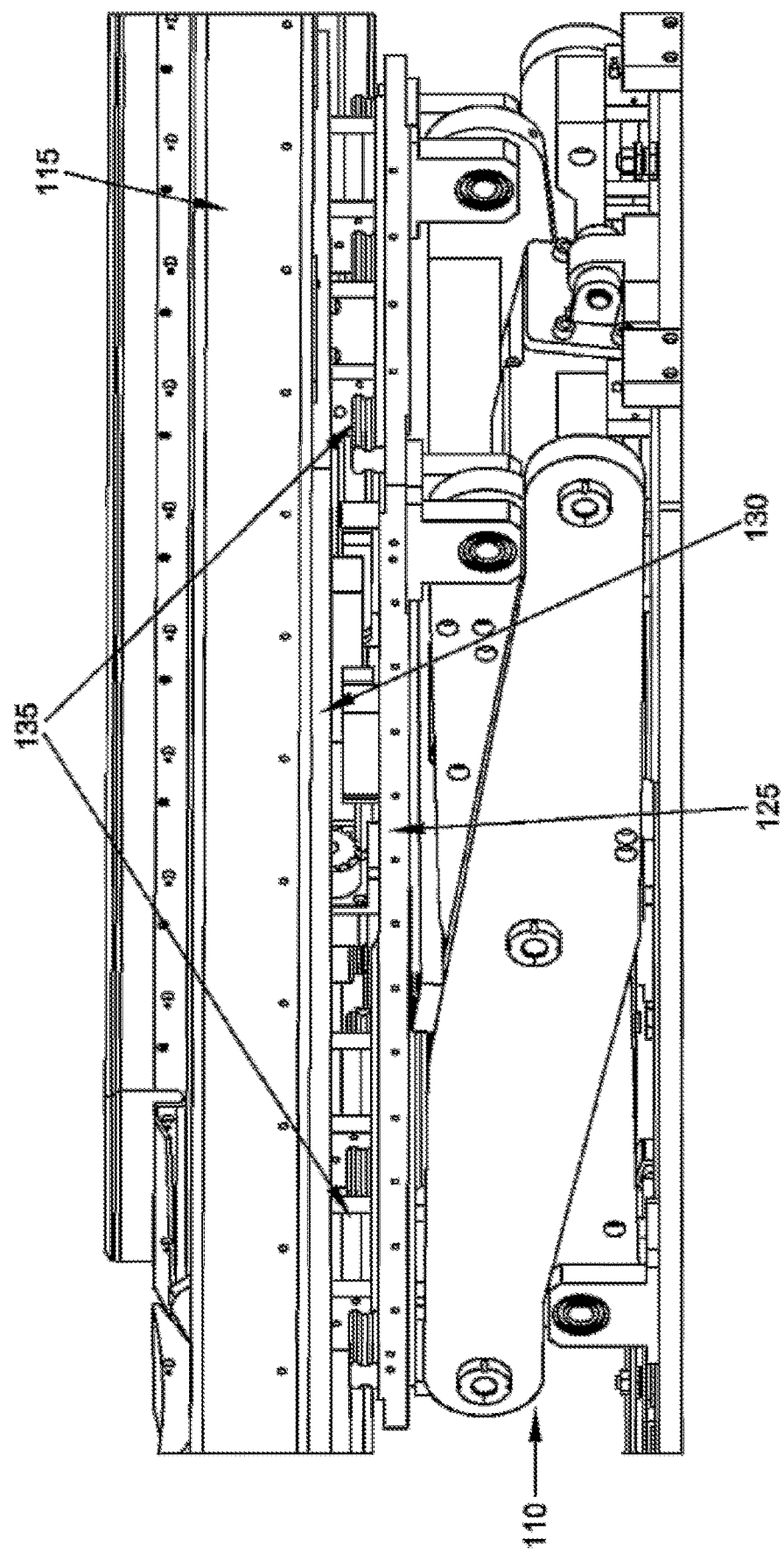
Figure 22:
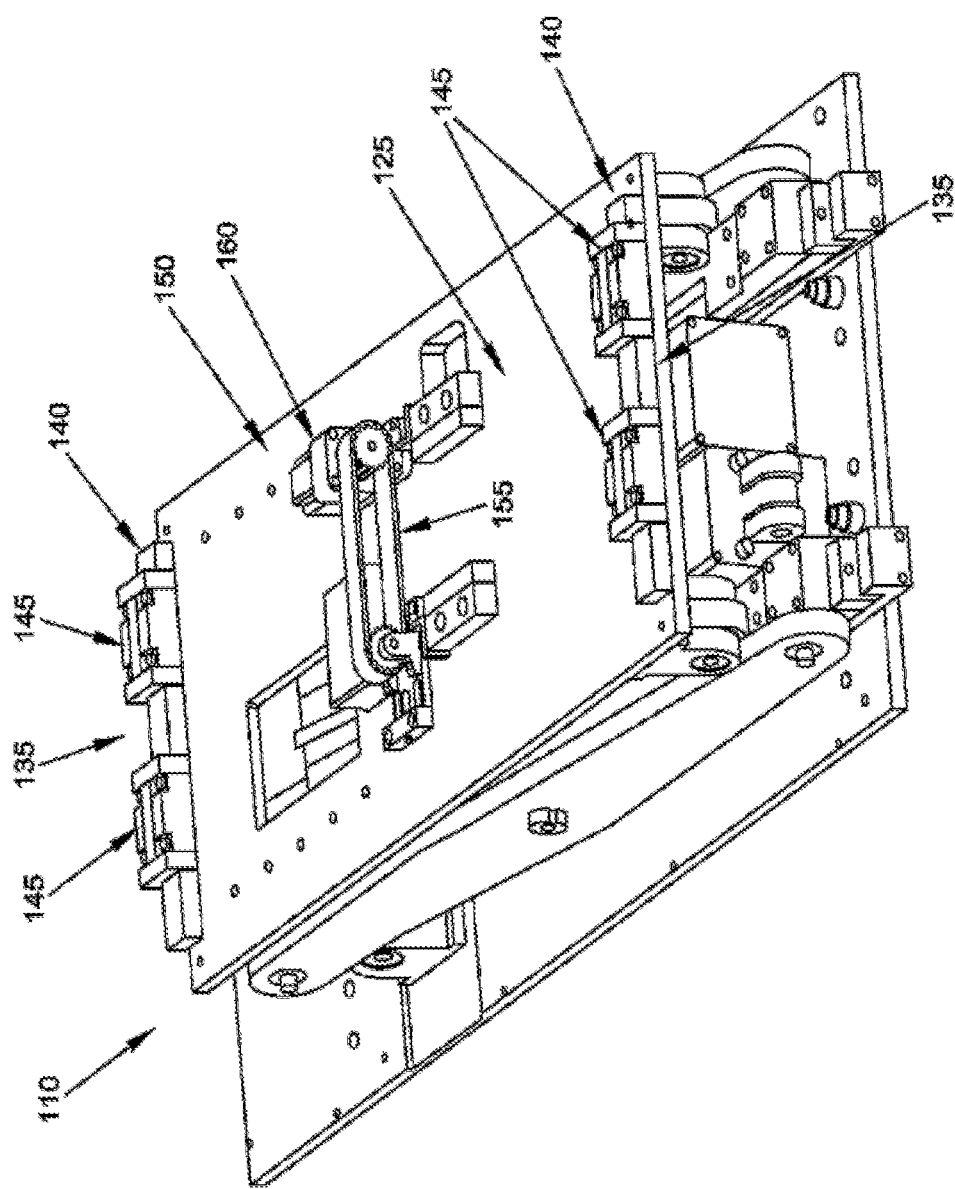
Figure 23:
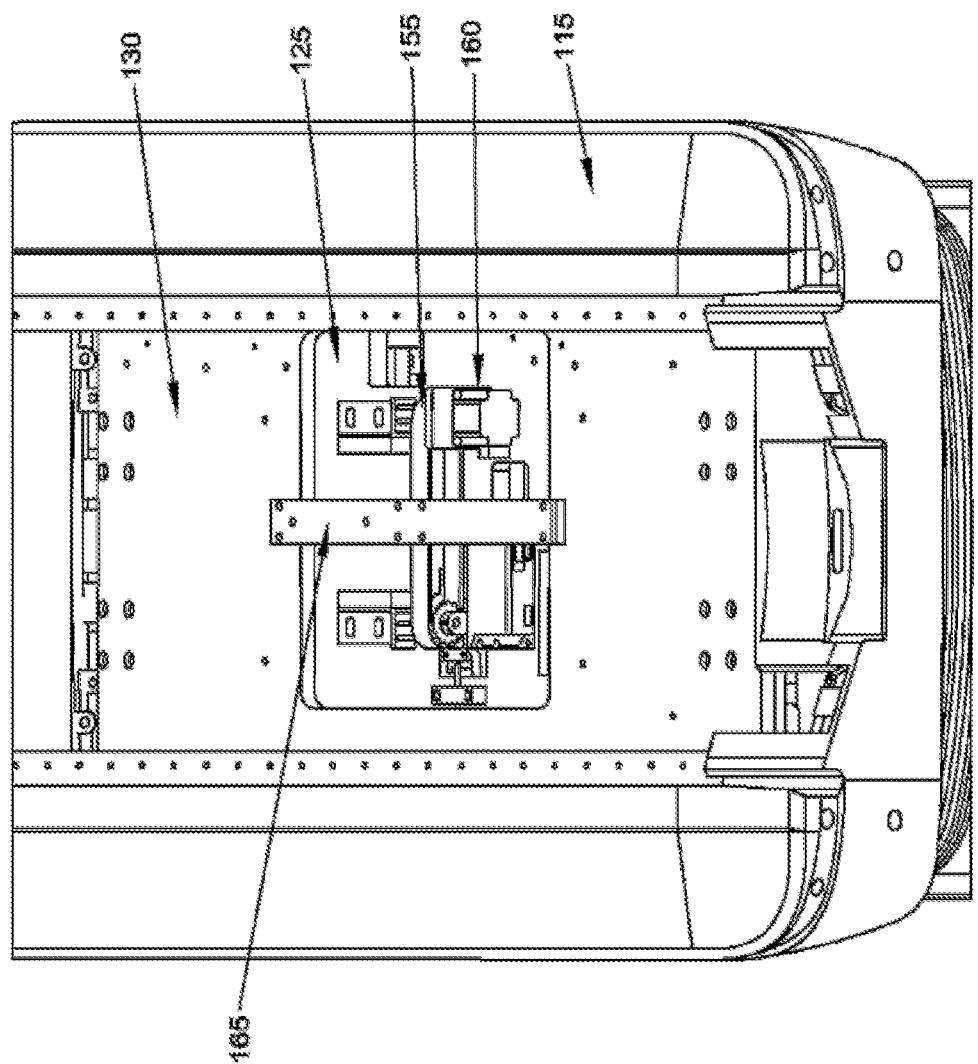
Figure 24:
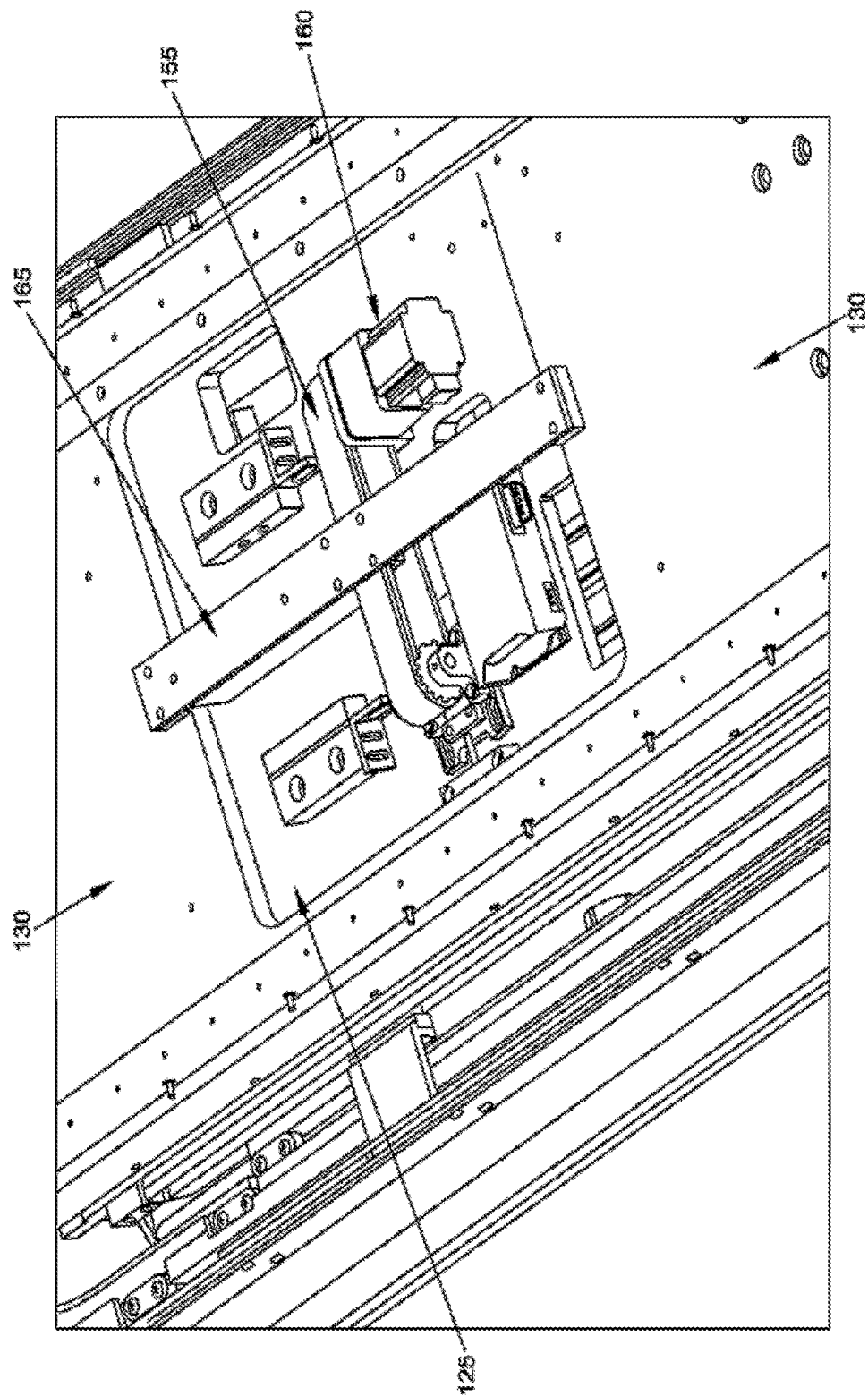
Figure 25:
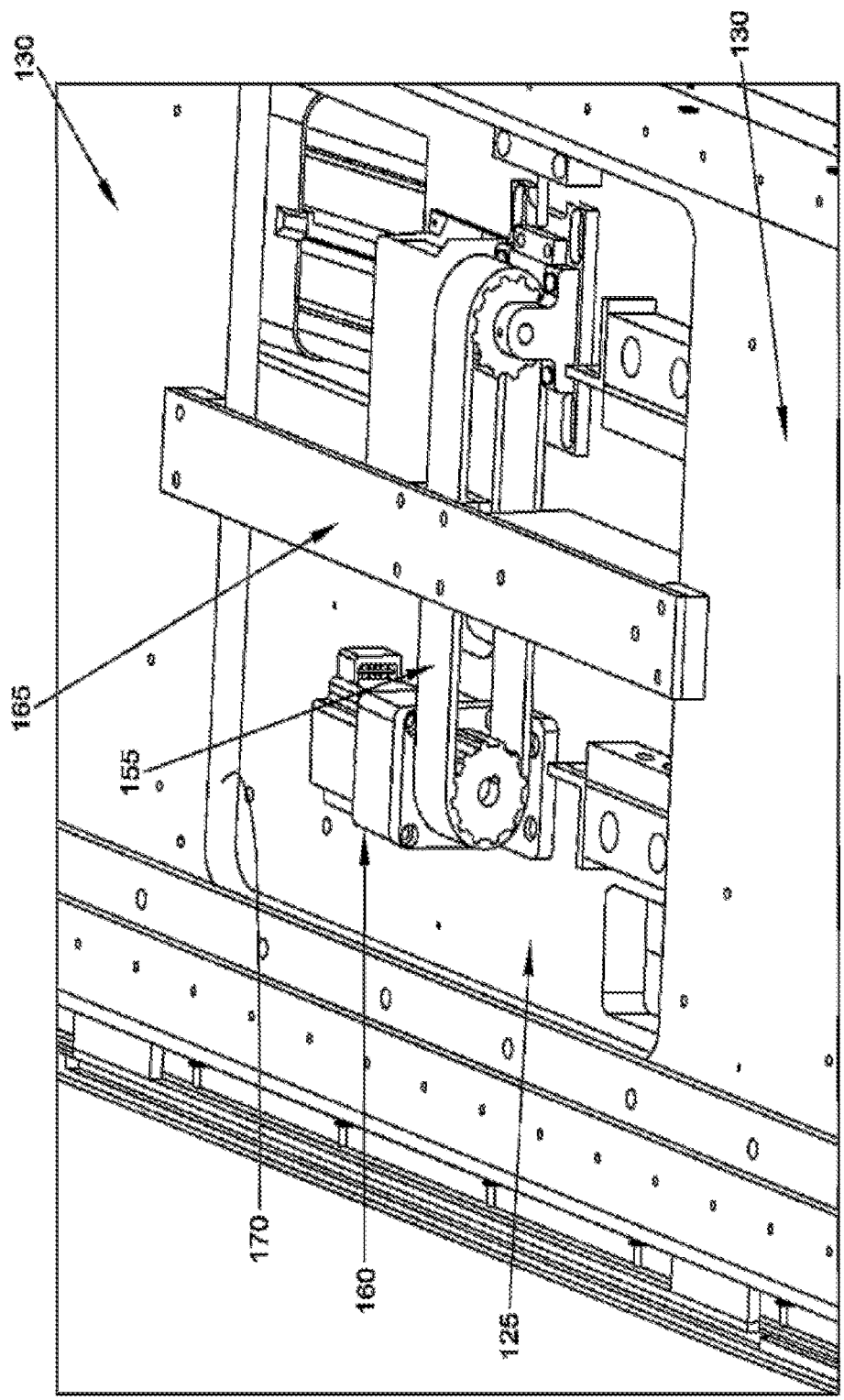
Figure 26:
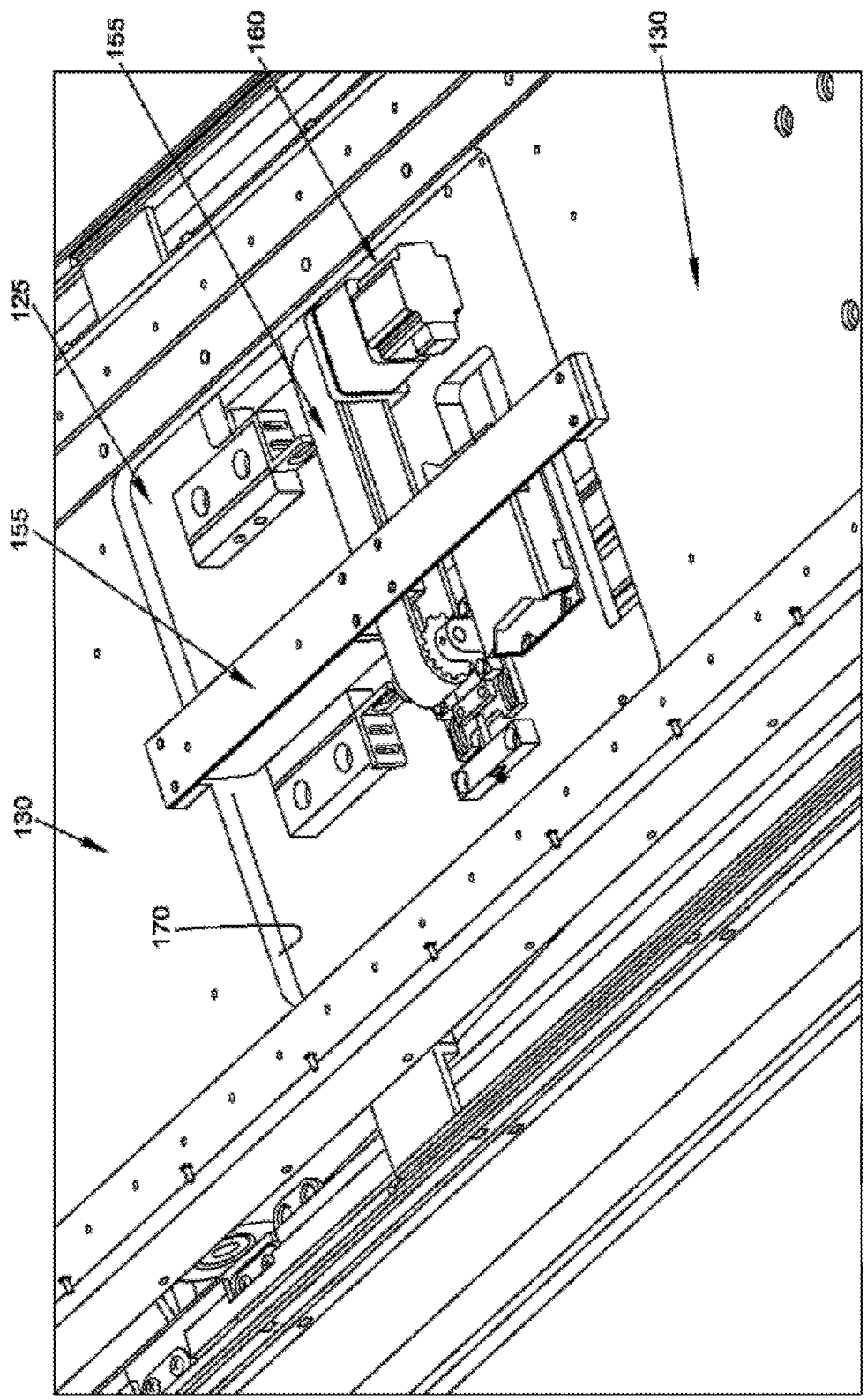

More particularly, and looking now at FIGS. 17-19, there is shown a novel scanning table 105. Scanning table 105 comprises a base 110 and a table top 115 slidably mounted to base 110, whereby to permit translation of table top 115 along the X-axis relative to base 110 (and hence relative to the longitudinal axis $A_C$ of center opening 20), as will hereinafter be discussed. A patient support platform 120 is slidably mounted to table top 115, whereby to permit translation of patient support platform 120 along the Z-axis relative to table top 115 (i.e., in order to advance/retract the patient into/out of center opening 20 of CT imaging system 5). Patient support platform 120 is formed out of an X-ray-transparent material so as to not impede imaging of the patient, and is moved relative to table top 115 in ways well known in the art.

Looking next at FIGS. 20-26, base 110 preferably comprises a base plate 125 mounted to the upper portion of base 110. Table top 115 comprises a table top plate 130 mounted to the bottom portion of table top 115. Table top plate 130 is configured to move along the X-axis relative to base plate 125. In one preferred form of the present invention, at least one linear guide 135 is disposed between base plate 125 and table top plate 130 for the purpose of facilitating movement of table top plate 130 relative to base plate 125. In one preferred form of the present invention, each linear guide 135 comprises a rail 140 fixedly mounted to base plate 125 and a pair of followers 145 which slidably ride on rail 140 and are mounted to table top plate 130. By virtue of this construction, table top plate 130 (and hence table top 115) can move along the X-axis relative to base plate 125 (and hence relative to base 110) when follower 145 slides along rail 140.

In one preferred form of the present invention, movement of table top plate 130 is effected through the use of an X-axis movement mechanism 150. More particularly, in one preferred form of the present invention, X-axis movement mechanism 150 comprises a drive belt 155 which is disposed perpendicular to the long axis (i.e., the Z-axis) of scanning table 105 and a motor 160 for turning drive belt 155. A bracket 165 is mounted to drive belt 155 such that when motor 160 is rotated in a first direction, bracket 165 moves relative to base plate 125 in a first direction along the X-axis, and when motor 160 is rotated in a second, opposite direction, bracket 165 moves relative to base plate 125 in a second, opposite direction along the X-axis. Bracket 165 is in turn mounted to table top plate 130 such that movement of drive belt 155 causes table top plate 130 (and hence table top 115) to move relative to base 110. In one preferred form of the present invention, table top plate 130 comprises an opening 170 and bracket 165 extends through opening 170 and is mounted to table top plate 130.

In use, when it is desired to move the patient (or the anatomy which is to be scanned) along the X-axis relative to center opening 20 of CT imaging system 5, X-axis movement mechanism 150 is operated so as to adjust the X-axis position of table top 115 relative to base 110 (and hence to adjust the X-axis disposition of the patient/anatomy relative to center opening 20). Scanning may then be effected by advancing patient support platform 120 along the Z-axis relative to base 110, whereby to insert the patient/anatomy into center opening 20 and thereby scan the patient/anatomy.

Minimizing The Length Of The Motorized
Scanning Table That Is Used To Scan A Patient In accordance with the present invention, there is also provided a new and improved motorized scanning table which is configured to move along the Y-axis (i.e., up and down) while also moving along the Z-axis, whereby to reduce the distance that the patient support platform must be cantilevered out over the fixed base of the motorized scanning table, while providing increased stability.

Figure 27:
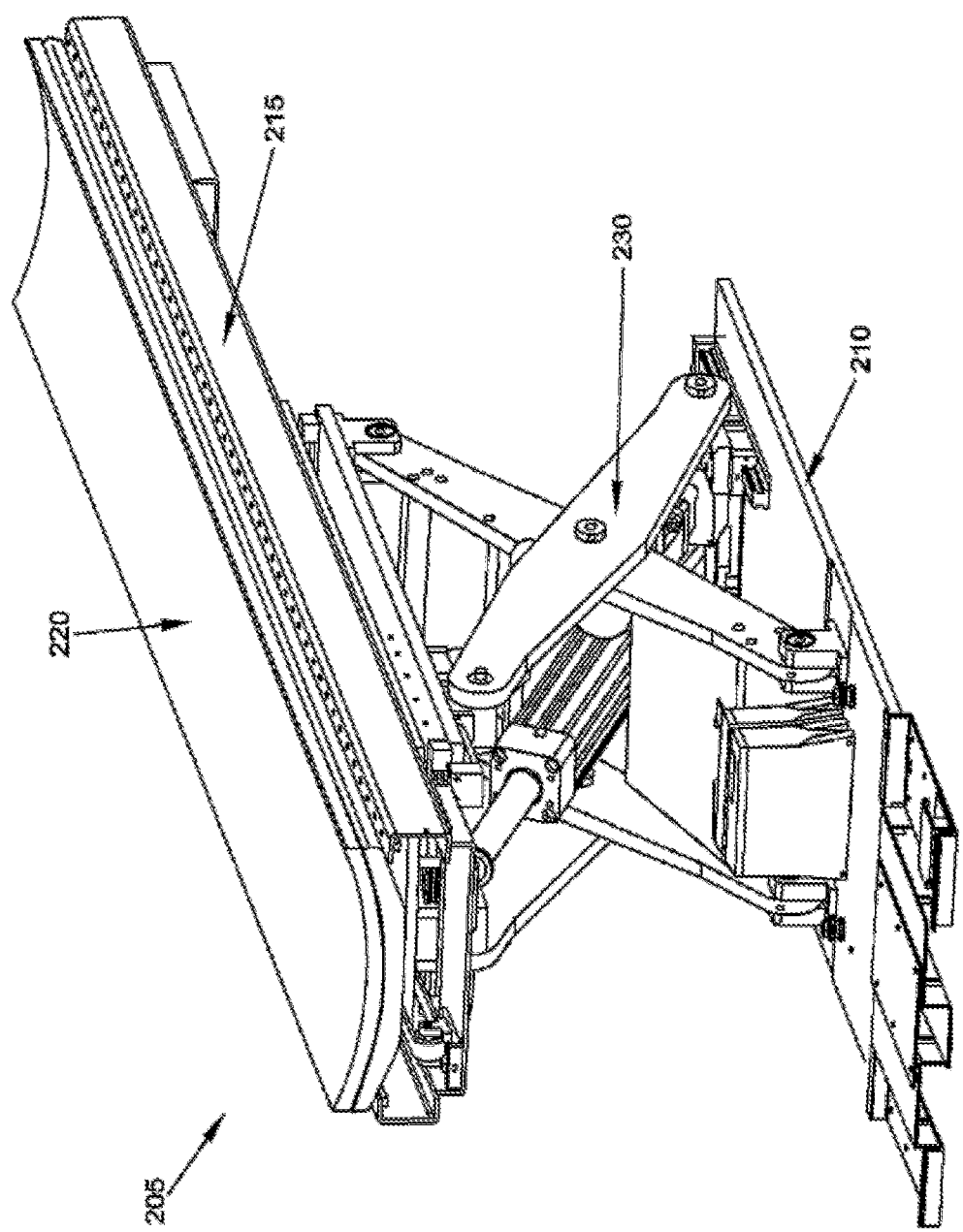
FIGS. 27-29 are schematic views showing another novel motorized scanning table formed in accordance with the present invention.
Figure 28:
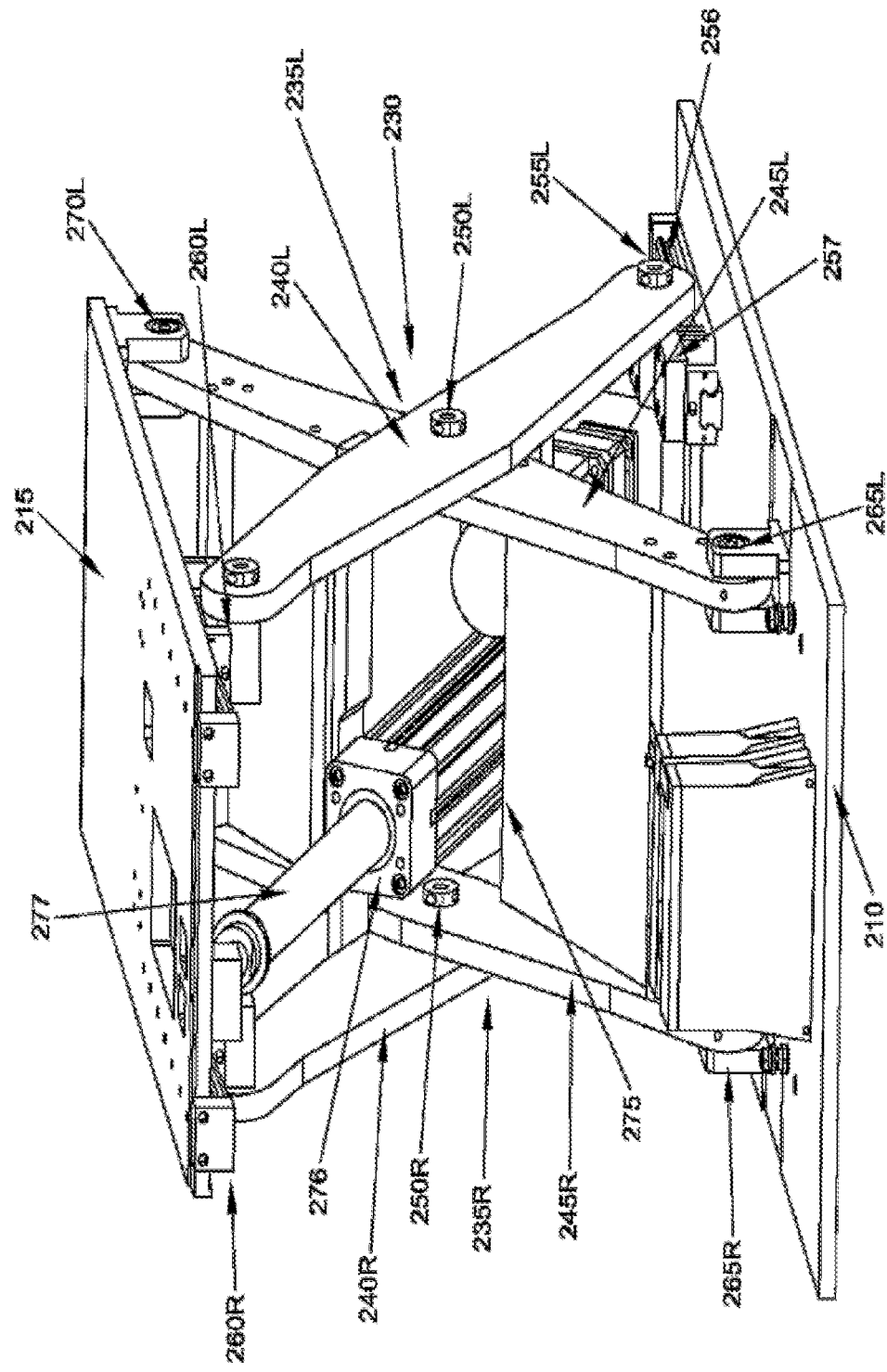
Figure 29:
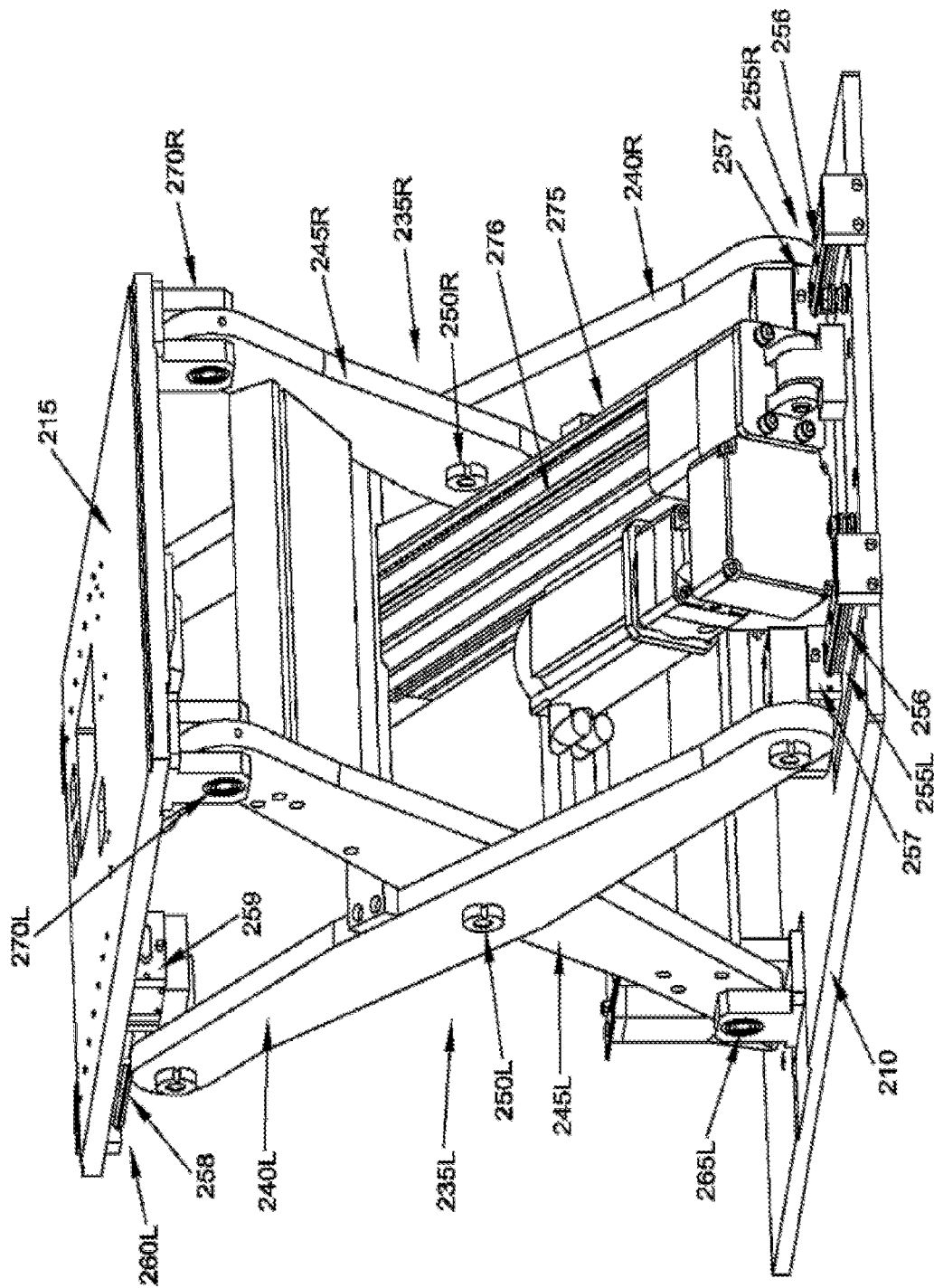
Figure 30:
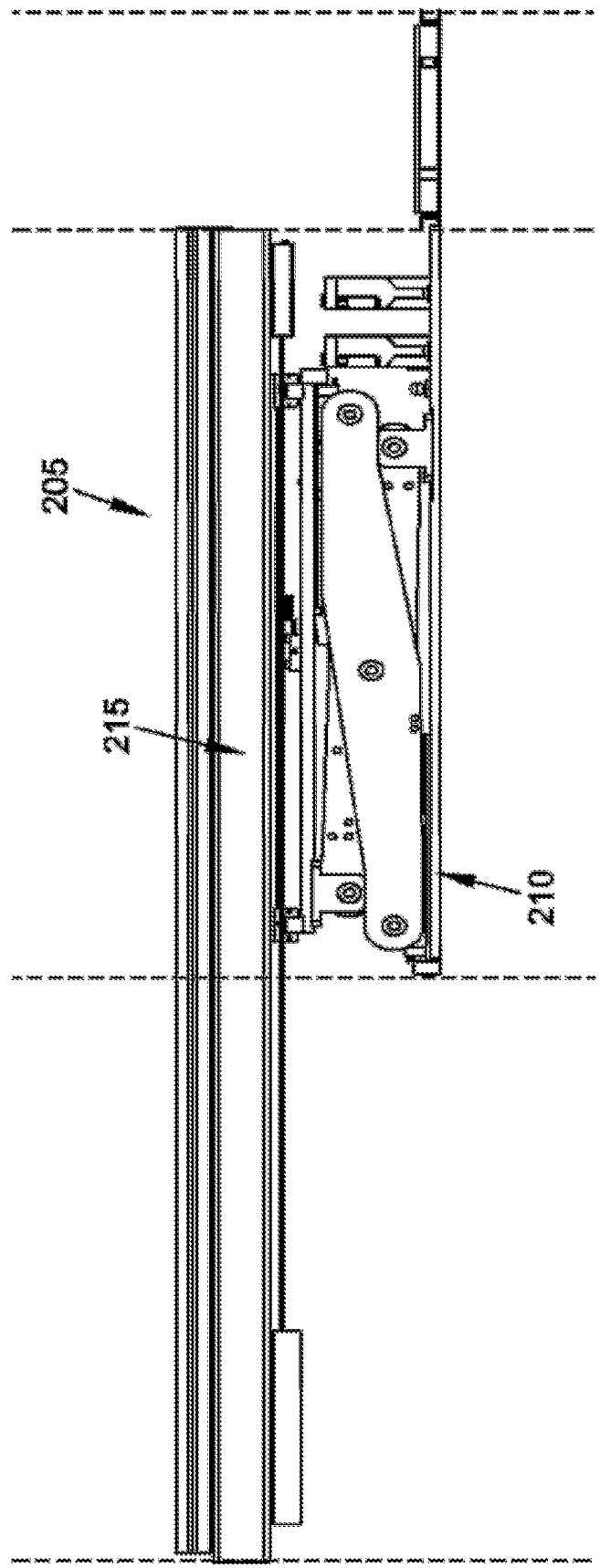
FIGS. 30-34 are schematic views showing how the novel motorized scanning table of FIGS. 27-29 is configured to move simultaneously along both the Y-axis and the Z-axis.
Figure 31:
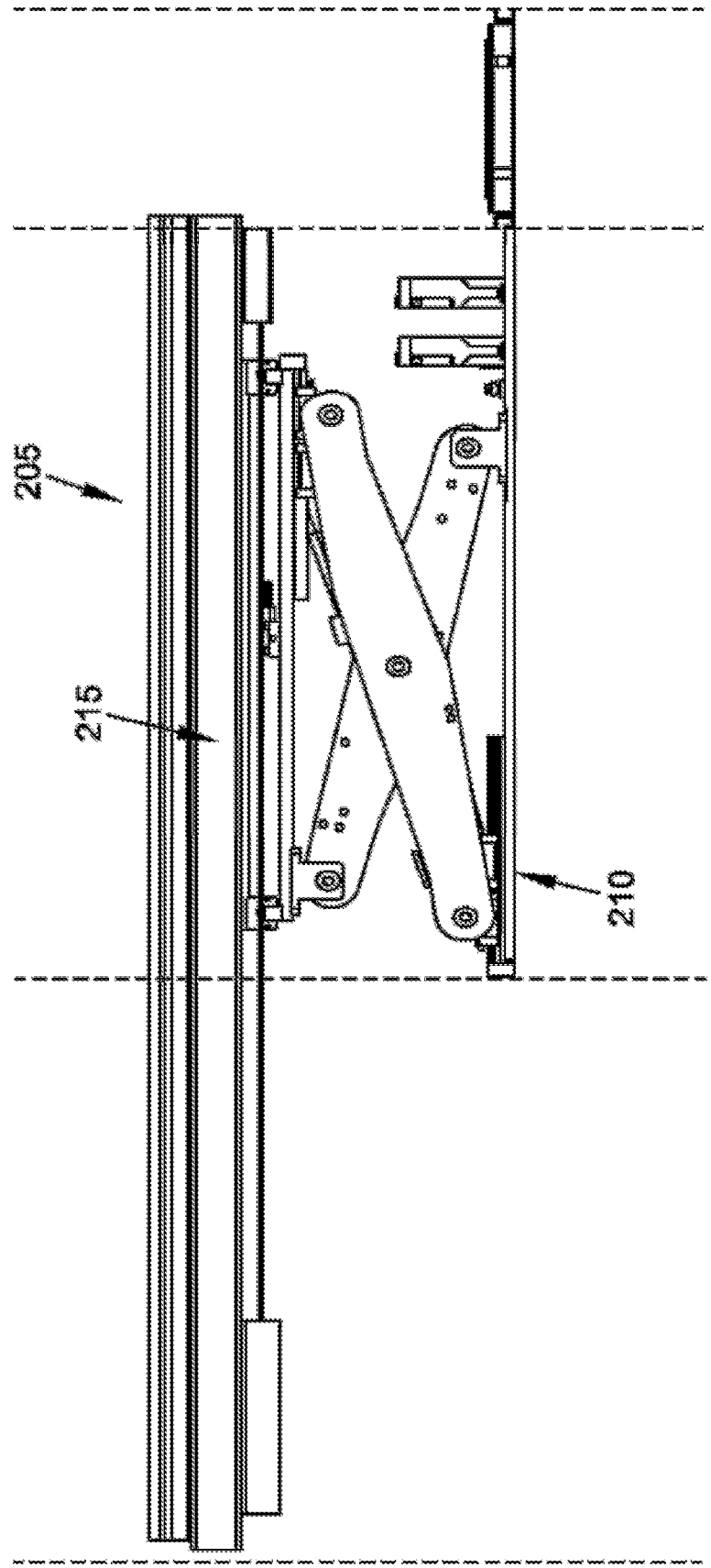

More particularly, and looking now at FIGS. 27-29, there is shown a novel motorized scanning table 205. Motorized scanning table 205 comprises a fixed base 210 and a table top 215 movably mounted to fixed base 210 so as to permit movement of table top 215 along the Y-axis and the Z-axis relative to fixed base 210, as will hereinafter be discussed. A patient support platform 220 is slidably mounted to table top 215, whereby to permit movement of patient support platform 220 along the Z-axis relative to fixed base 210 (i.e., to advance/retract the patient into/out of central opening 20 of CT imaging system 5). Patient support platform 220 is formed out of an X-ray-transparent material so as to not impede imaging of the patient, and is moved relative to table top 215 in ways well known in the art.

A novel scissor mount 230 is disposed between fixed base 210 and table top 215 in order to move table top 215 in the Y-axis and Z-axis relative to fixed base 210, as will hereinafter be discussed. Scissor mount 230 preferably comprises two scissor pairs 235R, 235L, one on each side of fixed base 210. Scissor pairs 235R, 235L comprise a pair of support arms 240R, 245R, and 240L, 245L, respectively.

Support arms 240R, 245R are connected to one another intermediate their length by a pivot mount 250R, and support arms 240L, 245L are connected together intermediate their length by a pivot mount 250L.

Support arms 240R and 240L are slidably mounted at one end to fixed base 210 by means of linear guides 255R, 255L, respectively, and are slidably mounted to table top 215 at their opposite ends by means of linear guides 260R, 260L, respectively. In one preferred form of the invention, linear guides 255R, 255L comprise rails 256 mounted to fixed base 210 and followers 257 mounted to support arms 240R, 240L, respectively, and linear guides 260R, 260L comprise rails 258 mounted to table top 215 and followers 259 mounted to support arms 240R, 240L, respectively. Support arms 245R and 245L are pivotally mounted to fixed base 210 via pivot mounts 265R, 265L, respectively, and pivotally mounted to table top 215 at their opposite ends via pivot mounts 270R, 270L, respectively.

A linear actuator 275 is disposed between fixed base 210 and table top 215. More particularly, the housing 276 of linear actuator 275 is pivotally mounted to fixed base 210 and the actuating rod 277 of linear actuator 275 is pivotally mounted to table top 215.

Figure 32:
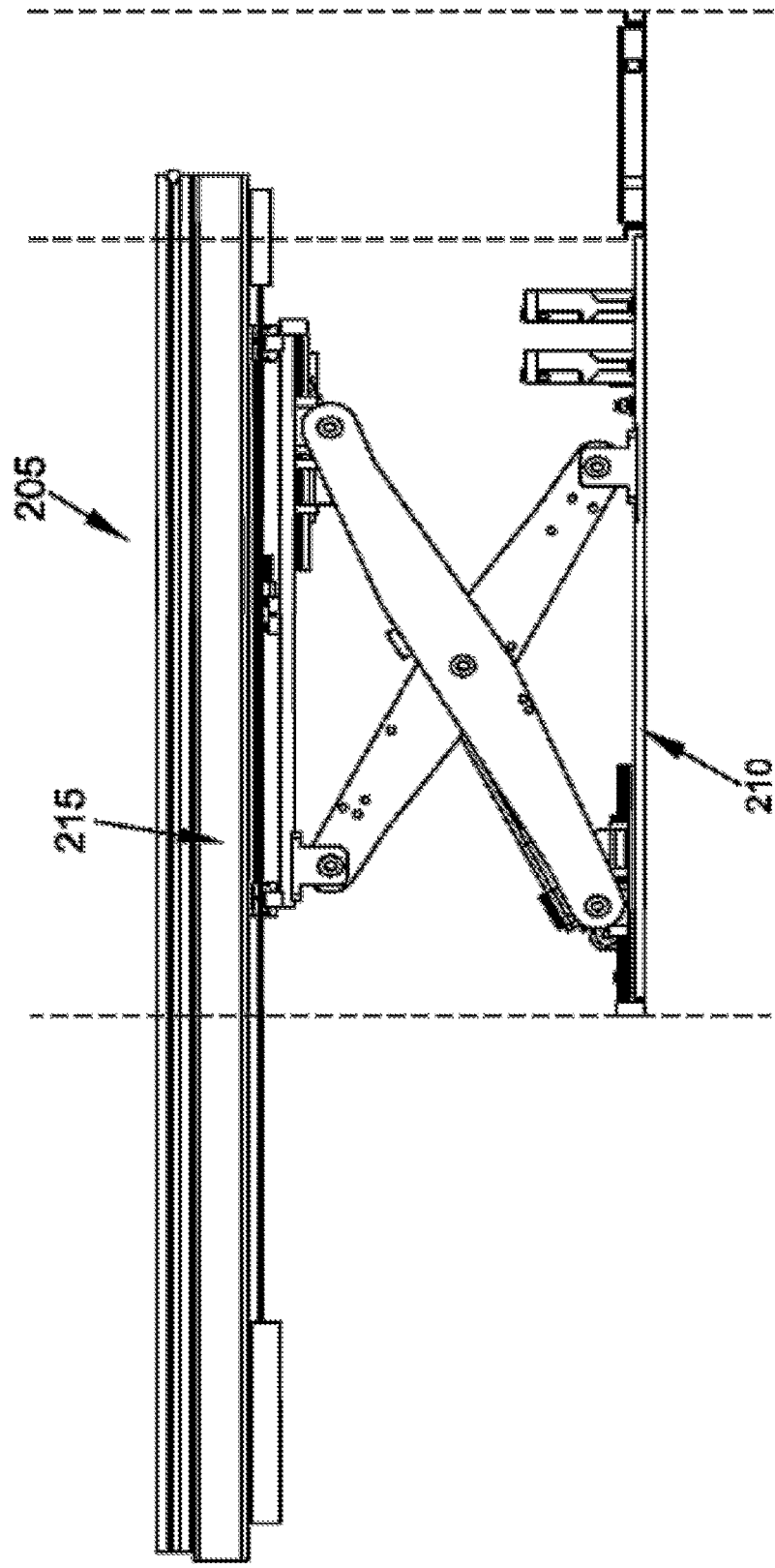
Figure 33:
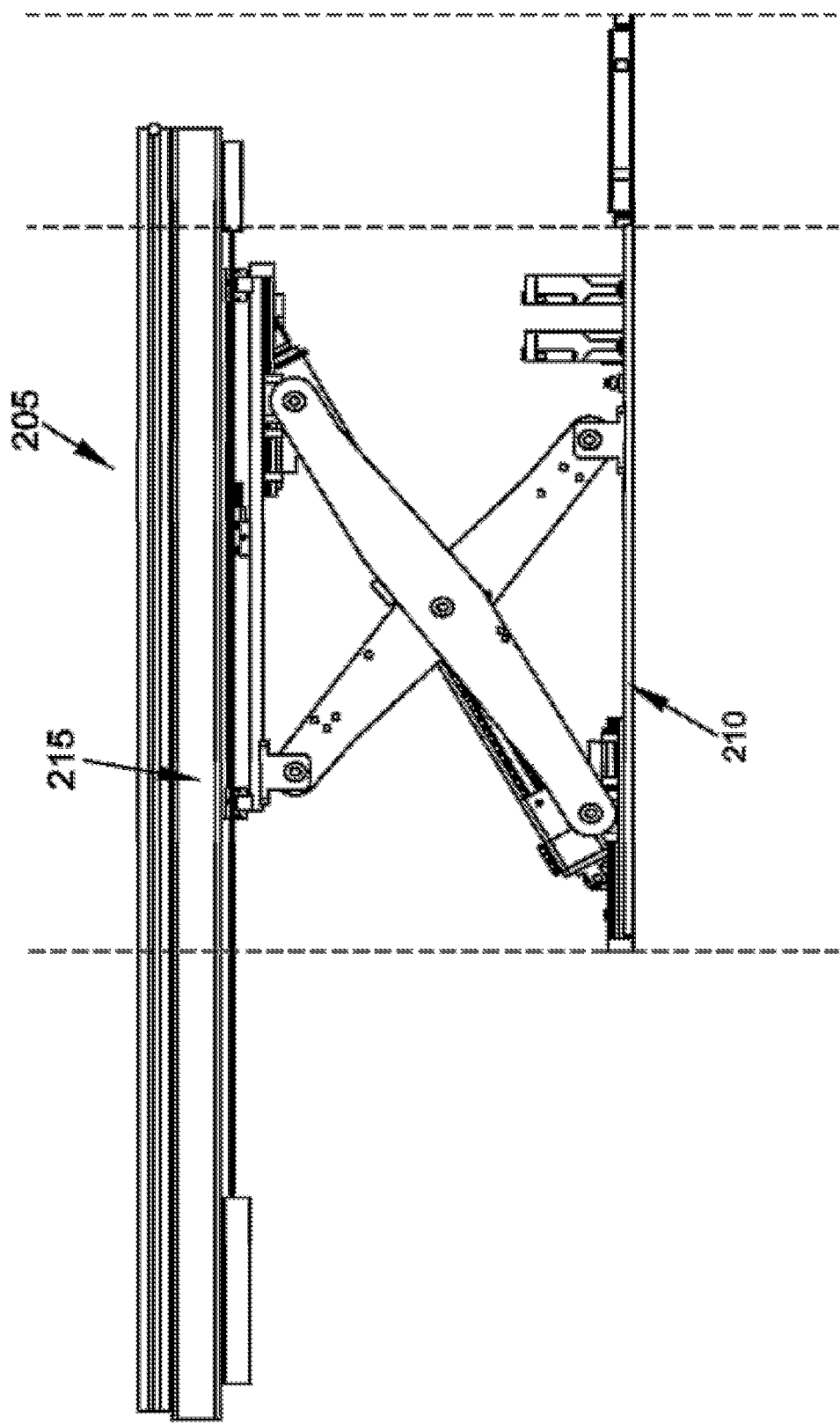
Figure 34:
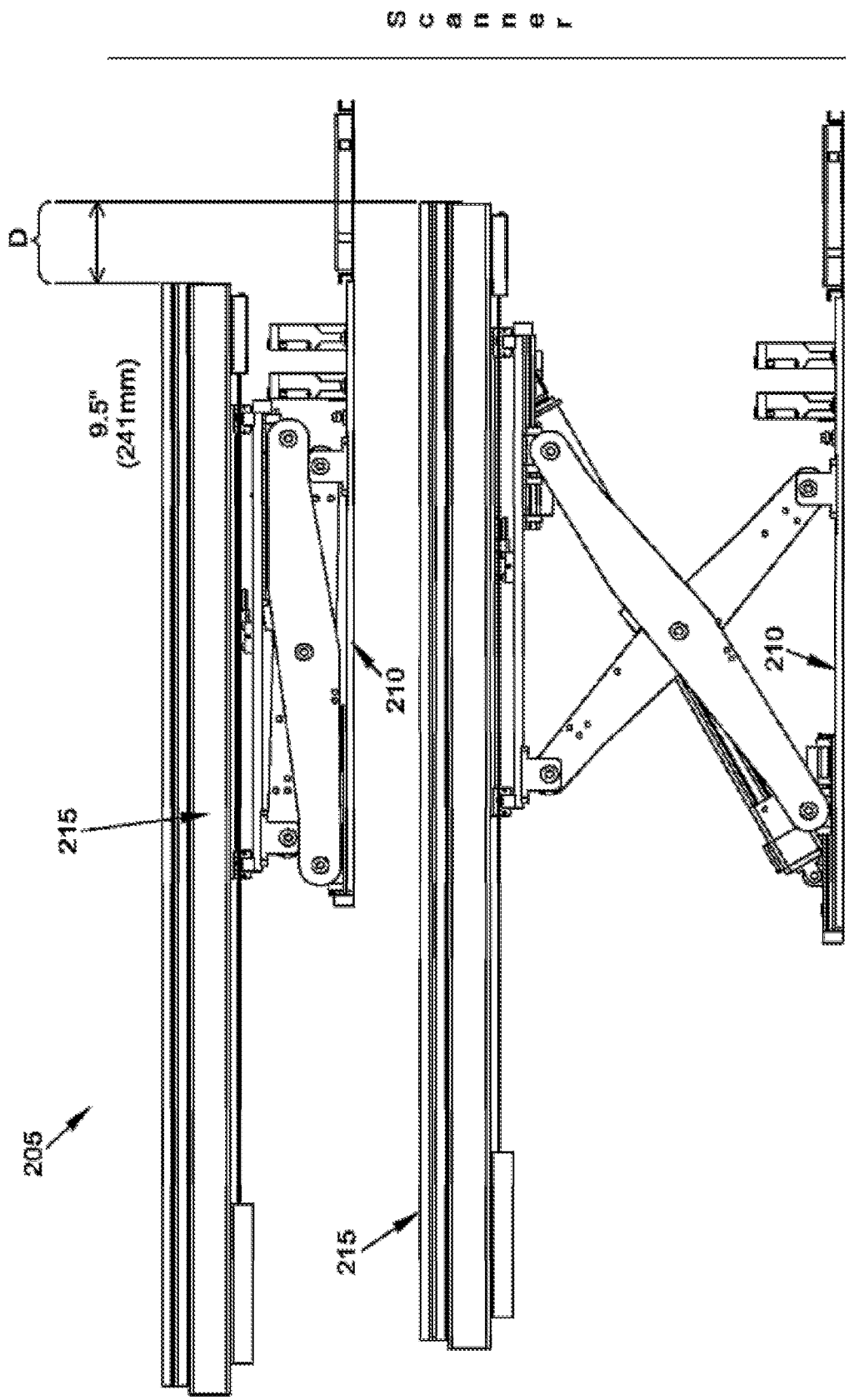

As a result of the forgoing construction, and looking now at FIGS. 30-34, table top 215 can be disposed close to fixed base 210 (FIG. 30) and then linear actuator 275 can be used to simultaneously move table top 215 along the Y-axis (i.e., to lift table top 215) while simultaneously moving table top 215 along the Z-axis (i.e., to advance table top 215 toward the scanner). See FIG. 31. More particularly, as the actuator rod 277 of linear actuator 275 is extended out of housing 276 of linear actuator 275, actuator rod 277 applies a force to table top 215, whereby to cause support arms 240R and 240L to slide along linear guides 255R, 255L relative to fixed base 225 in one direction and to slide along linear guides 260R, 260L relative to table top 215 in the opposite direction (FIGS. 32 and 33). As a result of this sliding movement of support arms 240R and 240L, table top 215 moves upward along the Y-axis and forward (i.e., toward the center opening 20 of CT imaging system 5) along the Z-axis. Thus it will be seen that as table top 215 is raised along the Y-axis, it is simultaneously moved along the Z-axis toward center opening 20 by a distance D (FIG. 34), thereby reducing the distance that patient support platform 220 must be cantilevered out over fixed base 210, and hence reducing the overall length required for patient support platform 220. At the same time, since support arms 240R, 245R are connected to one another intermediate their length via pivot mount 250R, and support arms 240L, 245L are connected together intermediate their length by pivot mount 250L, support arms 240R, 240L reinforce one another, thereby providing improved stability to motorized scanning table 205.

Figure 35:
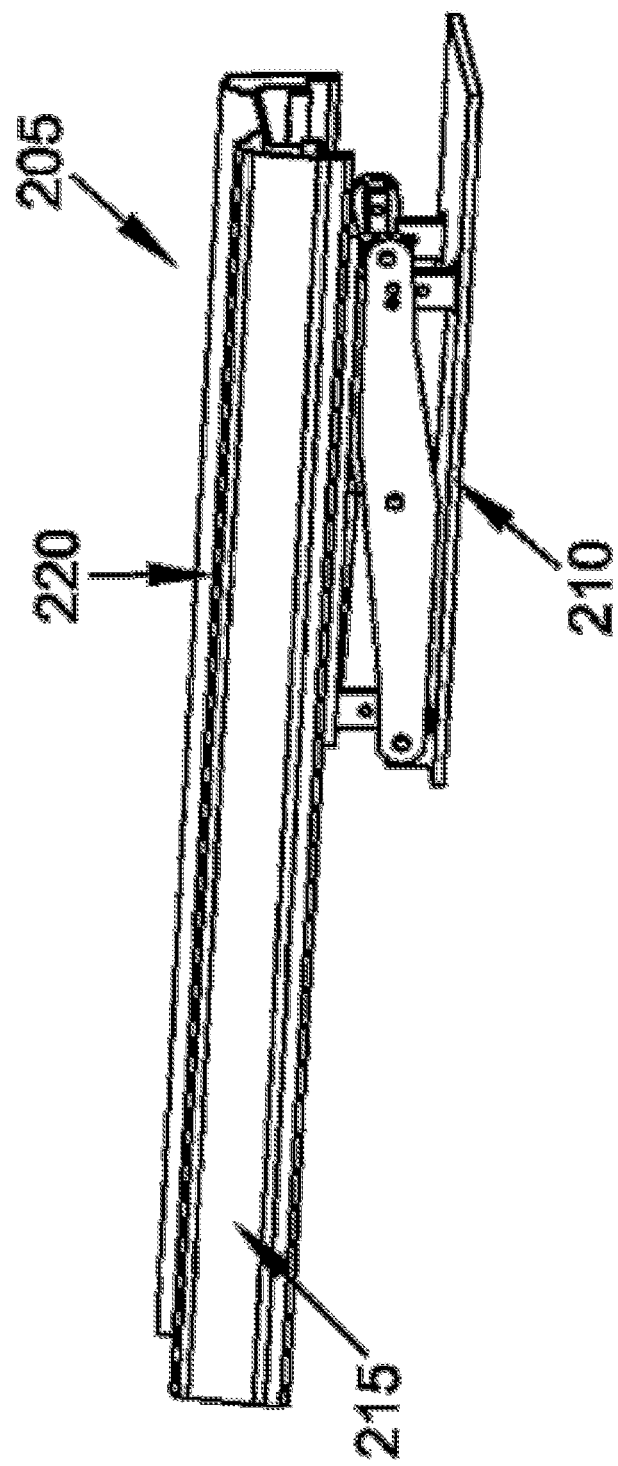
FIGS. 35-37 are schematic views showing movement of the table top of the motorized scanning table relative to the fixed base of the motorized scanning table along both the Y-axis and the Z-axis, and movement of the patient support platform of the motorized scanning table along the Z-axis.
Figure 36:
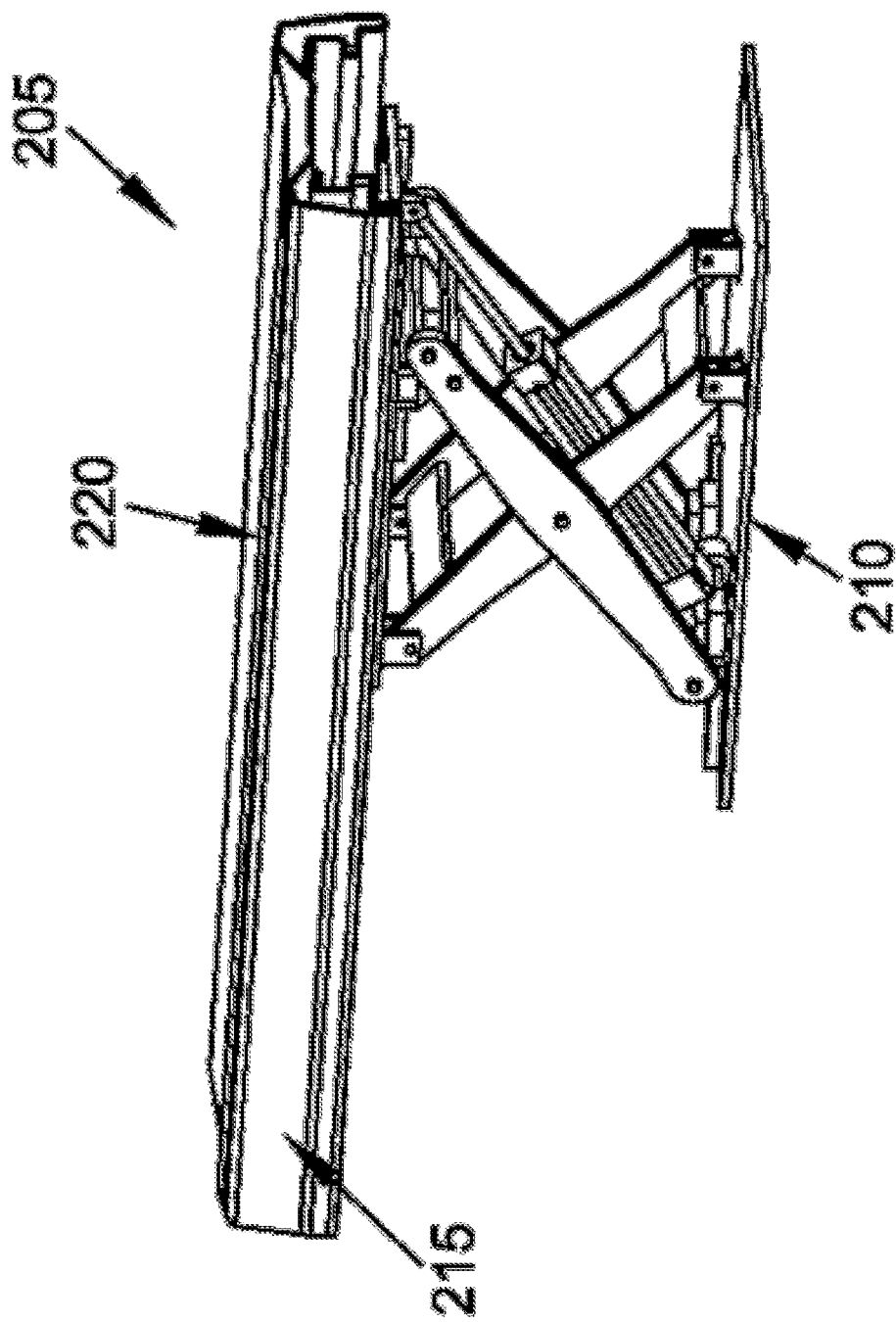
Figure 37:
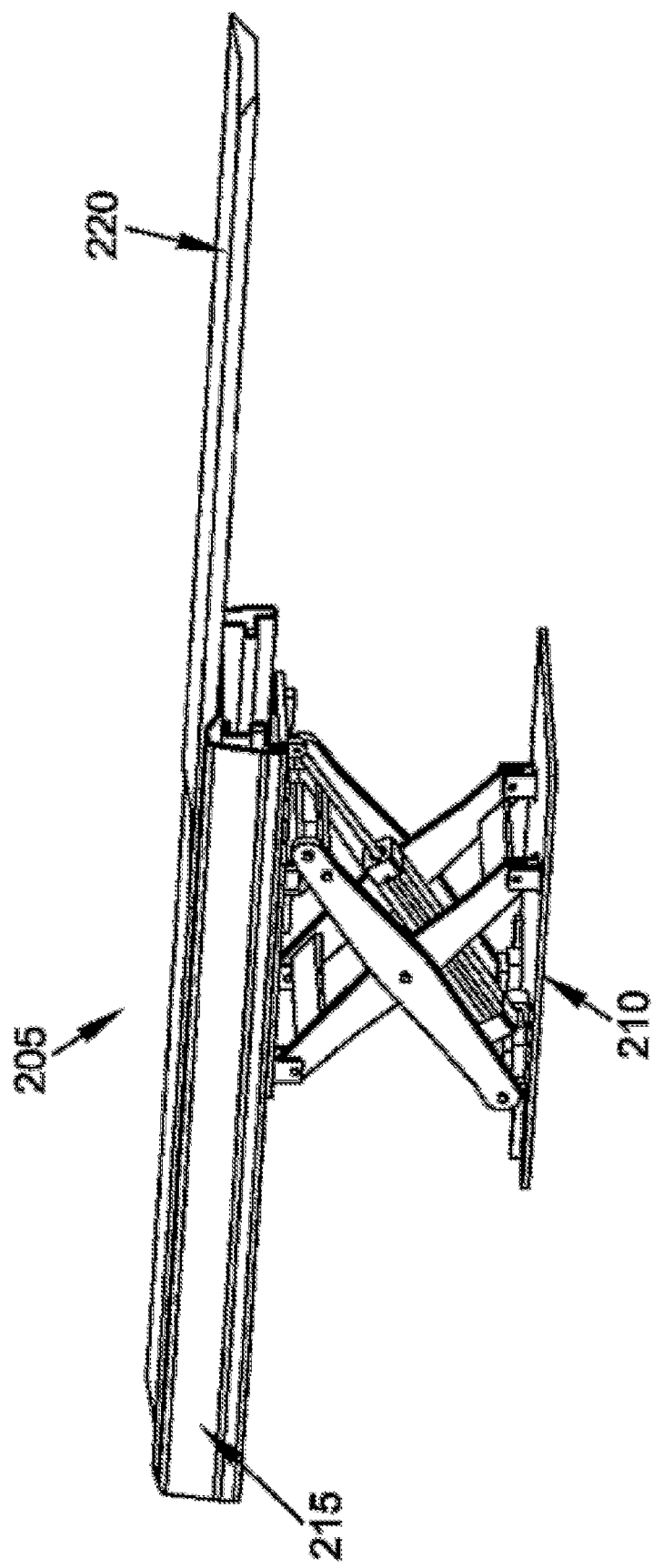

FIGS. 35-37 show how table top 215 can be simultaneously moved in the Y-axis and Z-axis relative to fixed base 210 by using improved scissor mount 230, and how patient support platform 220 can be extended along the Z-axis relative to table top 215.

Application to Other Types of Scanning Systems

It should be appreciated that the present invention is not limited to use in medical applications or, indeed, to use with CT machines. Thus, for example, the present invention may be used in connection with CT machines used for non-medical applications, e.g., with CT machines used to scan inanimate objects. Furthermore, the present invention may be used with non-CT-type scanning systems. Thus, for example, the present invention may be used in conjunction with SPECT machines, MRI machines, PET machines, X-ray machines, etc., i.e., wherever the scanning machine requires adjustment of the disposition of the object to be scanned relative to the scanning machine.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. A novel scanning table for use with a scanning machine, the novel scanning table comprising:
   a fixed base;
   a movable table top movably mounted to the fixed base for permitting the movable table top to be simultaneously moved along the Z-axis and the Y-axis relative to the fixed base; and
   a movement mechanism for moving the movable table top simultaneously along the Z-axis and the Y-axis relative to the fixed base, wherein the movement mechanism comprises (i) at least one support arm, wherein the at least one support arm is slidably mounted to the fixed base at one end of the support arm and is slidably mounted to the movable table top at the other end of the support arm, and (ii) an actuating element configured to be moved between an extended position and a retracted position, wherein the actuating element is pivotally mounted to the fixed base at one end of the actuating element and is pivotally mounted to the movable table top at the other end of the actuating element.

2. A novel scanning table according to claim 1 wherein at least one linear guide is disposed between the fixed base and the movable table top so as to enable controlled movement of the movable table top relative to the fixed base.

3. A novel scanning table according to claim 2 wherein the at least one linear guide comprises a rail secured to the fixed base and at least one follower which slidably rides on the rail and is secured to the movable table top.

4. A novel scanning table according to claim 3 wherein the fixed base comprises a base plate, the movable table top comprises a table top plate, and further wherein the rail is mounted to the base plate and the at least one follower is mounted to the table top plate.

5. A novel scanning table according to claim 4 further comprising an X-axis movement mechanism for selectively moving the movable table top relative to the fixed base.

6. A novel scanning table according to claim 5 wherein the X-axis movement mechanism comprises a drive belt supported by the fixed base, and a bracket secured to the drive belt and secured to the movable table top.

7. A novel scanning table according to claim 6 wherein the X-axis movement mechanism further comprises a motor for turning the drive belt.

8. A novel scanning table according to claim 1 wherein at least a portion of the scanning table is formed out of an X-ray transparent material.

9. A novel scanning table according to claim 1 wherein the scanning table further comprises a movable patient support platform movably mounted to the movable table top for permitting the movable patient support platform to be moved along the Z-axis relative to the movable table top.

10. A system comprising:
an imaging system; and
a scanning table comprising:
a fixed base;
a movable table top movably mounted to the fixed base for permitting the movable table top to be simultaneously moved along the Z-axis and the Y-axis relative to the fixed base; and
a movement mechanism for moving the movable table top simultaneously along the Z-axis and the Y-axis relative to the fixed base, wherein the movement mechanism comprises (i) at least one support arm, wherein the at least one support arm is slidably mounted to the fixed base at one end of the support arm and is slidably mounted to the movable table top at the other end of the support arm, and (ii) an actuating element configured to be moved between an extended position and a retracted position, wherein the actuating element is pivotally mounted to the fixed base at one end of the actuating element and is pivotally mounted to the movable table top at the other end of the actuating element.

11. A system according to claim 10 wherein at least one linear guide is disposed between the fixed base and the movable table top so as to enable controlled movement of the movable table top relative to the fixed base.

12. A system according to claim 11 wherein the at least one linear guide comprises a rail secured to the fixed base and at least one follower which slidably rides on the rail and is secured to the movable table top.

13. A system according to claim 12 wherein the fixed base comprises a base plate, the movable table top comprises a table top plate, and further wherein the rail is mounted to the base plate and the at least one follower is mounted to the table top plate.

14. A system according to claim 13 further comprising an X-axis movement mechanism for selectively moving the movable table top relative to the fixed base.

15. A system according to claim 14 wherein the X-axis movement mechanism comprises a drive belt supported by the fixed base, and a bracket secured to the drive belt and secured to the movable table top.

16. A system according to claim 15 wherein the X-axis movement mechanism further comprises a motor for turning the drive belt.

17. A system according to claim 10 wherein at least a portion of the scanning table is formed out of an X-ray transparent material.

18. A system according to claim 10 wherein the scanning table further comprises a movable patient support platform movably mounted to the movable table top for permitting the movable patient support platform to be moved along the Z-axis relative to the movable table top.

19. A method for scanning a patient, the method comprising:
providing an imaging system and providing a scanning table, the scanning table comprising:
a fixed base;
a movable table top movably mounted to the fixed base for permitting the movable table top to be simultaneously moved along the Z-axis and the Y-axis relative to the fixed base; and
a movement mechanism for moving the movable table top simultaneously along the Z-axis and the Y-axis relative to the fixed base, wherein the movement mechanism comprises (i) at least one support arm, wherein the at least one support arm is slidably mounted to the fixed base at one end of the support arm and is slidably mounted to the movable table top at the other end of the support arm, and (ii) an actuating element configured to be moved between an extended position and a retracted position, wherein the actuating element is pivotally mounted to the fixed base at one end of the actuating element and is pivotally mounted to the movable table top at the other end of the actuating element;
positioning the patient on the movable table top;
extending the actuating element to move moving the movable table top relative to the fixed base so as to adjust the disposition of the patient relative to the imaging system; and
using the imaging system to scan the patient.

20. A method according to claim 19 wherein at least one linear guide is disposed between the fixed base and the movable table top so as to enable controlled movement of the movable table top relative to the fixed base.

21. A method according to claim 20 wherein the at least one linear guide comprises a rail secured to the fixed base and at least one follower which slidably rides on the rail and is secured to the movable table top.

22. A method according to claim 21 wherein the fixed base comprises a base plate, the movable table top comprises a table top plate, and further wherein the rail is mounted to the base plate and the at least one follower is mounted to the table top plate.

23. A method according to claim 22 further comprising an X-axis movement mechanism for selectively moving the movable table top relative to the fixed base.

24. A method according to claim 23 wherein the X-axis movement mechanism comprises a drive belt supported by the fixed base, and a bracket secured to the drive belt and secured to the movable table top.

25. A method according to claim 24 wherein the X-axis movement mechanism further comprises a motor for turning the drive belt.

26. A method according to claim 19 wherein at least a portion of the scanning table is formed out of an X-ray transparent material.

27. A method according to claim 19 wherein the scanning table further comprises a movable patient support platform movably mounted to the movable table top for permitting the movable patient support platform to be moved along the Z-axis relative to the movable table top.

* * * * *